US012004853B2

United States Patent
Stahmann et al.

(10) Patent No.: US 12,004,853 B2
(45) Date of Patent: *Jun. 11, 2024

(54) SYSTEMS AND METHODS FOR DISAMBIGUATION OF POSTURE

(71) Applicant: Cardiac Pacemakers, Inc., St. Paul, MN (US)

(72) Inventors: Jeffrey E. Stahmann, Ramsey, MN (US); John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 199 days.

This patent is subject to a terminal disclaimer.

(21) Appl. No.: 16/041,923

(22) Filed: Jul. 23, 2018

(65) Prior Publication Data

US 2019/0029567 A1 Jan. 31, 2019

Related U.S. Application Data

(60) Provisional application No. 62/537,047, filed on Jul. 26, 2017.

(51) Int. Cl.
*A61B 5/11* (2006.01)
*A61B 5/145* (2006.01)
(Continued)

(52) U.S. Cl.
CPC ........ *A61B 5/1116* (2013.01); *A61B 5/14503* (2013.01); *A61B 5/14546* (2013.01);
(Continued)

(58) Field of Classification Search
None
See application file for complete search history.

(56) References Cited

U.S. PATENT DOCUMENTS 556,421 A    3/1896 Judge
4,200,110 A  4/1980 Peterson et al.
(Continued)

FOREIGN PATENT DOCUMENTS

CN    102333478    1/2012
CN    109381195    1/2023
(Continued)

OTHER PUBLICATIONS

Shirreffs, S. M., & Maughan, R. J. (1994). The effect of posture change on blood volume, serum potassium and whole body electrical impedance. European Journal of Applied Physiology and Occupational Physiology, 69(5), 461-463. doi: 10.1007/bf00865413 (Year: 1994).*

(Continued)

*Primary Examiner* — Yi-Shan Yang
*Assistant Examiner* — Samuel C Kim
(74) *Attorney, Agent, or Firm* — Pauly, DeVries Smith & Deffner LLC

(57) ABSTRACT

Embodiments include medical device systems, medical devices, including accelerometers and chemical sensors, and methods of using the same to determine the posture of a patient. In an embodiment, a medical device system herein includes an accelerometer configured to generate a signal reflecting a position of a patient, a chemical sensor configured to generate a signal reflecting physiological analyte data of the patient and a controller in electrical communication with the accelerometer and the chemical sensor. The controller can be configured to determine a posture of the patient using the position signal generated by the accelerometer and the signal generated by the chemical sensor. Other embodiments are also included herein.

2 Claims, 9 Drawing Sheets

(51) Int. Cl.
*A61N 1/05* (2006.01)
*A61N 1/365* (2006.01)
*A61N 1/368* (2006.01)
*A61N 1/37* (2006.01)

(52) U.S. Cl.
CPC ......... *A61B 5/1118* (2013.01); *A61B 5/14532* (2013.01); *A61B 2562/0219* (2013.01); *A61N 1/056* (2013.01); *A61N 1/365* (2013.01); *A61N 1/368* (2013.01); *A61N 1/3702* (2013.01)

(56) References Cited

U.S. PATENT DOCUMENTS

| | | |
|---|---|---|
| 4,321,057 A | 3/1982 | Buckles |
| 4,344,438 A | 8/1982 | Schultz et al. |
| 4,399,099 A | 8/1983 | Buckles |
| 4,680,268 A | 7/1987 | Clark |
| 4,704,029 A | 11/1987 | Van Heuvelen |
| 4,721,677 A | 1/1988 | Clark |
| 4,750,494 A | 6/1988 | King |
| 4,750,495 A | 6/1988 | Moore et al. |
| 4,890,621 A | 1/1990 | Hakky |
| 4,903,701 A | 2/1990 | Moore |
| 4,981,779 A | 1/1991 | Wagner |
| 5,001,054 A | 3/1991 | Wagner |
| 5,040,533 A | 8/1991 | Fearnot |
| 5,090,326 A | 2/1992 | Altenau et al. |
| 5,209,231 A | 5/1993 | Cote et al. |
| 5,267,151 A | 11/1993 | Ham et al. |
| 5,275,171 A | 1/1994 | Barcel |
| 5,312,439 A | 5/1994 | Loeb |
| 5,312,454 A | 5/1994 | Roline et al. |
| 5,330,718 A | 7/1994 | Hui et al. |
| 5,333,609 A | 8/1994 | Bedingham et al. |
| 5,342,406 A | 8/1994 | Thompson |
| 5,342,789 A | 8/1994 | Chick et al. |
| 5,355,880 A * | 10/1994 | Thomas ............... A61B 5/6826 600/326 |
| 5,378,432 A | 1/1995 | Bankert et al. |
| 5,419,329 A | 5/1995 | Smith et al. |
| 5,457,535 A | 10/1995 | Schmidtke et al. |
| 5,476,434 A * | 12/1995 | Kalb .................. A61B 5/14507 600/30 |
| 5,553,616 A | 9/1996 | Ham et al. |
| 5,556,421 A | 9/1996 | Prutchi et al. |
| 5,560,356 A | 10/1996 | Peyman |
| 5,605,152 A | 2/1997 | Slate et al. |
| 5,607,644 A | 3/1997 | Olstein et al. |
| 5,660,163 A | 8/1997 | Schulman et al. |
| 5,728,281 A | 3/1998 | Holmstrom et al. |
| 5,730,125 A | 3/1998 | Prutchi et al. |
| 5,741,211 A | 4/1998 | Renirie et al. |
| 5,797,898 A | 8/1998 | Santini et al. |
| 5,830,138 A | 11/1998 | Wilson |
| 5,833,603 A | 11/1998 | Kovacs et al. |
| 5,854,078 A | 12/1998 | Asher |
| 5,871,442 A | 2/1999 | Madarasz et al. |
| 5,902,326 A | 5/1999 | Lessar et al. |
| 5,958,782 A | 9/1999 | Bentsen et al. |
| 5,995,860 A | 11/1999 | Sun et al. |
| 6,002,954 A | 12/1999 | Van Antwerp et al. |
| 6,011,984 A | 1/2000 | Van Antwerp et al. |
| 6,040,194 A | 3/2000 | Chick et al. |
| 6,049,727 A | 4/2000 | Crothall |
| 6,070,093 A | 5/2000 | Oosta et al. |
| 6,097,139 A | 8/2000 | Tuck et al. |
| 6,122,536 A | 9/2000 | Sun et al. |
| 6,123,861 A | 9/2000 | Santini et al. |
| 6,125,290 A | 9/2000 | Miesel |
| 6,125,291 A | 9/2000 | Miesel et al. |
| 6,134,459 A | 10/2000 | Roberts et al. |
| 6,144,866 A | 11/2000 | Miesel et al. |
| 6,163,714 A | 12/2000 | Stanley et al. |
| 6,175,642 B1 | 1/2001 | Gobbi et al. |
| 6,187,599 B1 | 2/2001 | Asher et al. |
| 6,216,022 B1 | 4/2001 | Tyrrell et al. |
| 6,219,137 B1 | 4/2001 | Vo-Dinh |
| 6,232,130 B1 | 5/2001 | Wolf |
| 6,236,870 B1 | 5/2001 | Madarasz et al. |
| 6,256,522 B1 | 7/2001 | Schultz |
| 6,267,724 B1 | 7/2001 | Taylor et al. |
| 6,268,161 B1 | 7/2001 | Han et al. |
| 6,277,627 B1 | 8/2001 | Hellinga |
| 6,304,766 B1 | 10/2001 | Colvin, Jr. |
| 6,330,464 B1 | 12/2001 | Colvin et al. |
| 6,343,223 B1 | 1/2002 | Chin et al. |
| 6,344,340 B1 | 2/2002 | Dibner et al. |
| 6,368,274 B1 | 4/2002 | Van Antwerp et al. |
| 6,383,767 B1 | 5/2002 | Polak |
| 6,438,397 B1 | 8/2002 | Bosquet et al. |
| 6,442,409 B1 | 8/2002 | Peyman |
| 6,454,710 B1 | 9/2002 | Ballerstadt et al. |
| 6,466,821 B1 | 10/2002 | Pianca et al. |
| 6,491,639 B1 | 12/2002 | Turcott |
| 6,491,666 B1 | 12/2002 | Santini, Jr. et al. |
| 6,505,059 B1 | 1/2003 | Kollias et al. |
| 6,521,446 B2 | 2/2003 | Hellinga |
| 6,527,762 B1 | 3/2003 | Santini, Jr. et al. |
| 6,544,800 B2 | 4/2003 | Asher |
| 6,551,838 B2 | 4/2003 | Santini, Jr. et al. |
| 6,579,690 B1 | 6/2003 | Bonnecaze et al. |
| 6,594,092 B2 | 7/2003 | Von et al. |
| 6,594,510 B2 | 7/2003 | Madarasz et al. |
| 6,602,521 B1 | 8/2003 | Ting et al. |
| 6,625,479 B1 | 9/2003 | Weber et al. |
| 6,666,821 B2 | 12/2003 | Keimel et al. |
| 6,671,527 B2 | 12/2003 | Petersson et al. |
| 6,673,596 B1 | 1/2004 | Sayler et al. |
| 6,682,938 B1 | 1/2004 | Satcher, Jr. et al. |
| 6,694,158 B2 | 2/2004 | Polak |
| 6,711,423 B2 | 3/2004 | Colvin |
| 6,731,976 B2 | 5/2004 | Penn et al. |
| RE38,525 E | 6/2004 | Stanley et al. |
| 6,766,183 B2 | 7/2004 | Walsh |
| 6,771,993 B2 | 8/2004 | Rule et al. |
| 6,800,451 B2 | 10/2004 | Daniloff et al. |
| 6,804,544 B2 | 10/2004 | Van Antwerp et al. |
| 6,814,490 B1 | 11/2004 | Suhm et al. |
| 6,815,162 B2 | 11/2004 | Boukherroub et al. |
| 6,835,553 B2 | 12/2004 | Han et al. |
| 6,855,556 B2 | 2/2005 | Amiss et al. |
| 6,875,208 B2 | 4/2005 | Santini, Jr. et al. |
| 6,885,881 B2 | 4/2005 | Leonhardt |
| 6,885,883 B2 | 4/2005 | Parris et al. |
| 6,893,545 B2 | 5/2005 | Gotoh et al. |
| 6,912,078 B2 | 6/2005 | Kudrle et al. |
| 6,918,873 B1 | 7/2005 | Millar et al. |
| 6,928,325 B2 | 8/2005 | Zhu et al. |
| 6,937,900 B1 | 8/2005 | Pianca et al. |
| 6,944,488 B2 | 9/2005 | Roberts |
| 6,952,603 B2 | 10/2005 | Gerber et al. |
| 6,957,094 B2 | 10/2005 | Chance et al. |
| 6,976,982 B2 | 12/2005 | Santini, Jr. et al. |
| 6,978,182 B2 | 12/2005 | Mazar et al. |
| 7,016,714 B2 | 3/2006 | Colvin, Jr. et al. |
| 7,039,446 B2 | 5/2006 | Ruchti et al. |
| 7,070,590 B1 | 7/2006 | Santini, Jr. et al. |
| 7,107,086 B2 | 9/2006 | Reihl et al. |
| 7,133,710 B2 | 11/2006 | Acosta et al. |
| 7,134,999 B2 | 11/2006 | Brauker et al. |
| 7,144,474 B1 | 12/2006 | Hansen et al. |
| 7,164,948 B2 | 1/2007 | Struble et al. |
| 7,166,871 B2 | 1/2007 | Erchak |
| 7,174,212 B1 | 2/2007 | Klehn et al. |
| 7,225,024 B2 | 5/2007 | Zhu et al. |
| 7,236,821 B2 | 6/2007 | Cates et al. |
| 7,410,616 B2 | 8/2008 | Santini, Jr. et al. |
| 7,447,533 B1 | 11/2008 | Fang et al. |
| 7,449,246 B2 | 11/2008 | Kim et al. |
| 7,450,980 B2 | 11/2008 | Kawanishi |
| 7,471,290 B2 | 12/2008 | Wang et al. |
| 7,577,470 B2 | 8/2009 | Shah et al. |
| 7,632,234 B2 | 12/2009 | Manda et al. |
| 7,633,356 B2 | 12/2009 | Hamet et al. |

(56) References Cited

U.S. PATENT DOCUMENTS

| | | | |
|---|---|---|---|
| 7,686,762 B1 | 3/2010 | Najafi et al. | |
| 7,761,130 B2 | 7/2010 | Simpson et al. | |
| 7,805,174 B2 | 9/2010 | Carpenter et al. | |
| 7,809,441 B2* | 10/2010 | Kane | A61N 1/37288 607/22 |
| 7,829,147 B2 | 11/2010 | Aitken et al. | |
| 7,890,171 B2 | 2/2011 | Zhu et al. | |
| 7,894,884 B2 | 2/2011 | Song et al. | |
| 8,126,554 B2 | 2/2012 | Kane et al. | |
| 8,131,364 B2 | 3/2012 | Zhu et al. | |
| 8,141,489 B2 | 3/2012 | Belanger et al. | |
| 8,160,670 B2 | 4/2012 | Ouyang et al. | |
| 8,165,840 B2 | 4/2012 | Hatlestad et al. | |
| 8,257,067 B2 | 9/2012 | Fukui et al. | |
| 8,290,592 B2 | 10/2012 | Michael et al. | |
| 8,303,511 B2 | 11/2012 | Eigler et al. | |
| 8,378,453 B2 | 2/2013 | Fedorov et al. | |
| 8,414,489 B2 | 4/2013 | Shah et al. | |
| 8,435,604 B2 | 5/2013 | Aitken et al. | |
| 8,527,067 B2 | 9/2013 | De Kock et al. | |
| 8,571,659 B2 | 10/2013 | Kane et al. | |
| 8,636,884 B2 | 1/2014 | Feldman et al. | |
| 8,710,625 B2 | 4/2014 | Fedorov et al. | |
| 8,765,060 B2 | 7/2014 | Buhlmann et al. | |
| 8,827,899 B2 | 9/2014 | Farr et al. | |
| 9,101,277 B2 | 8/2015 | Doerr | |
| 9,326,707 B2 | 5/2016 | McGarraugh | |
| 9,357,968 B2 | 6/2016 | Hauer et al. | |
| 9,399,076 B2 | 7/2016 | Yu et al. | |
| 9,693,714 B2 | 7/2017 | Dehennis et al. | |
| 10,194,808 B1 | 2/2019 | Thompson et al. | |
| 10,667,745 B2 | 6/2020 | Anker et al. | |
| 10,716,500 B2* | 7/2020 | Stahmann | A61B 5/6861 |
| 10,952,621 B2 | 3/2021 | Kane et al. | |
| 11,089,983 B2 | 8/2021 | Li et al. | |
| 11,129,557 B2 | 9/2021 | Li et al. | |
| 11,439,304 B2 | 9/2022 | Stahmann et al. | |
| 11,571,151 B2 | 2/2023 | Kane et al. | |
| 2002/0016535 A1 | 2/2002 | Martin et al. | |
| 2002/0026108 A1 | 2/2002 | Colvin | |
| 2002/0033260 A1 | 3/2002 | Lungwitz et al. | |
| 2002/0033454 A1 | 3/2002 | Cheng et al. | |
| 2002/0035317 A1 | 3/2002 | Cheng et al. | |
| 2002/0095075 A1 | 7/2002 | Madarasz et al. | |
| 2002/0127626 A1 | 9/2002 | Daniloff et al. | |
| 2002/0151812 A1* | 10/2002 | Scheiner | A61B 7/04 600/528 |
| 2003/0100040 A1 | 5/2003 | Bonnecaze et al. | |
| 2003/0100822 A1 | 5/2003 | Lew et al. | |
| 2003/0114735 A1 | 6/2003 | Silver et al. | |
| 2003/0191376 A1 | 10/2003 | Samuels et al. | |
| 2003/0208113 A1 | 11/2003 | Mault et al. | |
| 2004/0023317 A1 | 2/2004 | Motamedi et al. | |
| 2004/0030365 A1 | 2/2004 | Rubin | |
| 2004/0059206 A1 | 3/2004 | Braig et al. | |
| 2004/0073100 A1 | 4/2004 | Ballerstadt et al. | |
| 2004/0087842 A1 | 5/2004 | Lakowicz et al. | |
| 2004/0100376 A1 | 5/2004 | Lye et al. | |
| 2004/0106953 A1 | 6/2004 | Yomtov et al. | |
| 2004/0132172 A1 | 7/2004 | Cunningham et al. | |
| 2004/0133079 A1 | 7/2004 | Mazar et al. | |
| 2004/0147034 A1 | 7/2004 | Gore et al. | |
| 2004/0161853 A1 | 8/2004 | Yang et al. | |
| 2004/0176669 A1 | 9/2004 | Colvin, Jr. | |
| 2004/0176672 A1 | 9/2004 | Silver et al. | |
| 2004/0180379 A1 | 9/2004 | Van Duyne et al. | |
| 2004/0180391 A1 | 9/2004 | Gratzl et al. | |
| 2004/0186359 A1 | 9/2004 | Beaudoin et al. | |
| 2004/0199062 A1 | 10/2004 | Petersson et al. | |
| 2004/0206916 A1 | 10/2004 | Colvin, Jr. et al. | |
| 2004/0215134 A1 | 10/2004 | Soykan et al. | |
| 2004/0249311 A1 | 12/2004 | Haar et al. | |
| 2004/0254438 A1 | 12/2004 | Chuck et al. | |
| 2004/0260162 A1 | 12/2004 | Rohleder et al. | |
| 2005/0027176 A1 | 2/2005 | Xie | |
| 2005/0033133 A1 | 2/2005 | Kraft | |
| 2005/0038329 A1 | 2/2005 | Morris et al. | |
| 2005/0042704 A1 | 2/2005 | Alarcon et al. | |
| 2005/0043894 A1 | 2/2005 | Fernandez | |
| 2005/0065464 A1 | 3/2005 | Talbot et al. | |
| 2005/0065556 A1 | 3/2005 | Reghabi et al. | |
| 2005/0070768 A1 | 3/2005 | Zhu et al. | |
| 2005/0070770 A1 | 3/2005 | Dirac et al. | |
| 2005/0070771 A1 | 3/2005 | Rule et al. | |
| 2005/0096587 A1 | 5/2005 | Santini et al. | |
| 2005/0107677 A1 | 5/2005 | Ward et al. | |
| 2005/0113657 A1 | 5/2005 | Alarcon et al. | |
| 2005/0113658 A1 | 5/2005 | Jacobson et al. | |
| 2005/0130249 A1 | 6/2005 | Parris et al. | |
| 2005/0137481 A1 | 6/2005 | Sheard et al. | |
| 2005/0148832 A1 | 7/2005 | Reghabi et al. | |
| 2005/0149139 A1 | 7/2005 | Plicchi et al. | |
| 2005/0154272 A1 | 7/2005 | Dirac et al. | |
| 2005/0221276 A1 | 10/2005 | Rozakis et al. | |
| 2005/0221277 A1 | 10/2005 | Kawanishi | |
| 2005/0228226 A1 | 10/2005 | Muckner | |
| 2006/0025748 A1 | 2/2006 | Ye | |
| 2006/0076236 A1 | 4/2006 | Shah et al. | |
| 2006/0217771 A1 | 9/2006 | Soykan et al. | |
| 2006/0229694 A1 | 10/2006 | Schulman et al. | |
| 2006/0253043 A1* | 11/2006 | Zhang | A61B 5/366 600/512 |
| 2006/0270923 A1 | 11/2006 | Brauker et al. | |
| 2007/0027495 A1 | 2/2007 | Gerber | |
| 2007/0118056 A1 | 5/2007 | Wang et al. | |
| 2007/0156194 A1* | 7/2007 | Wang | A61N 1/3756 607/25 |
| 2007/0219628 A1 | 9/2007 | Shanley et al. | |
| 2007/0252713 A1 | 11/2007 | Rondoni et al. | |
| 2007/0270674 A1 | 11/2007 | Kane et al. | |
| 2007/0270675 A1 | 11/2007 | Kane et al. | |
| 2007/0275035 A1 | 11/2007 | Herman et al. | |
| 2008/0033260 A1 | 2/2008 | Sheppard et al. | |
| 2008/0046080 A1 | 2/2008 | Vanden et al. | |
| 2008/0077190 A1 | 3/2008 | Kane | |
| 2008/0082001 A1 | 4/2008 | Hatlestad et al. | |
| 2008/0086177 A1* | 4/2008 | Min | A61B 5/349 607/25 |
| 2008/0152283 A1 | 6/2008 | Nielsen et al. | |
| 2008/0294047 A1* | 11/2008 | Kodama | A61B 8/08 600/449 |
| 2008/0294209 A1 | 11/2008 | Thompson et al. | |
| 2009/0018425 A1 | 1/2009 | Ouyang et al. | |
| 2009/0024045 A1* | 1/2009 | Prakash | A61N 1/36514 600/523 |
| 2009/0076353 A1 | 3/2009 | Carpenter et al. | |
| 2009/0124875 A1 | 5/2009 | Bentsen et al. | |
| 2009/0156920 A1 | 6/2009 | Kotzan et al. | |
| 2009/0221885 A1 | 9/2009 | Hall et al. | |
| 2009/0259407 A1 | 10/2009 | Gerlitz | |
| 2009/0312973 A1 | 12/2009 | Hatlestad et al. | |
| 2010/0057057 A1 | 3/2010 | Hayter et al. | |
| 2010/0059792 A1 | 3/2010 | Shur et al. | |
| 2010/0119760 A1 | 5/2010 | Kirk et al. | |
| 2010/0149544 A1 | 6/2010 | Ghislain | |
| 2010/0280578 A1* | 11/2010 | Skelton | A61N 1/3605 607/62 |
| 2010/0292634 A1 | 11/2010 | Bilmes et al. | |
| 2011/0024307 A1 | 2/2011 | Simpson et al. | |
| 2011/0098547 A1 | 4/2011 | Zhu et al. | |
| 2011/0130666 A1 | 6/2011 | Dong et al. | |
| 2012/0059232 A1 | 3/2012 | Gross et al. | |
| 2013/0060105 A1 | 3/2013 | Shah et al. | |
| 2013/0150689 A1 | 6/2013 | Shaw-klein | |
| 2013/0184599 A1 | 7/2013 | Friedman et al. | |
| 2013/0197332 A1 | 8/2013 | Lucisano et al. | |
| 2013/0338727 A1* | 12/2013 | Mokelke | A61B 5/1116 607/45 |
| 2014/0018644 A1 | 1/2014 | Colvin et al. | |
| 2014/0091945 A1 | 4/2014 | Rivas et al. | |
| 2014/0155710 A1 | 6/2014 | Rowland et al. | |
| 2014/0187878 A1 | 7/2014 | Emken et al. | |
| 2014/0276164 A1 | 9/2014 | Thakur et al. | |
| 2014/0286875 A1 | 9/2014 | Gamsey et al. | |

(56) References Cited

U.S. PATENT DOCUMENTS

| | | | |
|---|---|---|---|
| 2014/0357964 | A1 | 12/2014 | Wisniewski et al. |
| 2014/0364758 | A1 | 12/2014 | Schindhelm et al. |
| 2015/0057509 | A1 | 2/2015 | Huffstetler et al. |
| 2015/0164383 | A1 | 6/2015 | Varsavsky et al. |
| 2015/0173655 | A1* | 6/2015 | Demmer ............... A61B 5/1118 600/595 |
| 2015/0352229 | A1 | 12/2015 | Brill et al. |
| 2016/0256063 | A1 | 9/2016 | Friedman et al. |
| 2016/0363550 | A1 | 12/2016 | Koo et al. |
| 2016/0374597 | A1 | 12/2016 | Stahmann |
| 2017/0000359 | A1 | 1/2017 | Kohli et al. |
| 2017/0215732 | A1 | 8/2017 | Genier et al. |
| 2017/0245788 | A1 | 8/2017 | Heikenfeld |
| 2018/0055426 | A1 | 3/2018 | Kane et al. |
| 2018/0153451 | A1 | 6/2018 | Heikenfeld et al. |
| 2018/0263511 | A1 | 9/2018 | Burnes et al. |
| 2018/0344218 | A1 | 12/2018 | Li et al. |
| 2018/0350468 | A1* | 12/2018 | Friedman ............... A61B 5/349 |
| 2018/0364207 | A1 | 12/2018 | Roberts et al. |
| 2019/0046032 | A1 | 2/2019 | Stahmann et al. |
| 2019/0125228 | A1 | 5/2019 | Kane et al. |
| 2019/0167112 | A1 | 6/2019 | Kane et al. |
| 2019/0167162 | A1 | 6/2019 | Li et al. |
| 2019/0336050 | A1 | 11/2019 | Deck et al. |
| 2020/0029904 | A1 | 1/2020 | Kim |
| 2021/0093235 | A1 | 4/2021 | Desousa et al. |
| 2021/0401564 | A1 | 12/2021 | Neuenfeldt et al. |
| 2022/0133177 | A1 | 5/2022 | Li et al. |
| 2022/0133178 | A1 | 5/2022 | Li et al. |
| 2022/0133234 | A1 | 5/2022 | Li et al. |

FOREIGN PATENT DOCUMENTS

| | | |
|---|---|---|
| EP | 3440999 | 2/2019 |
| EP | 3492014 | 6/2019 |
| EP | 3409203 | 4/2021 |
| EP | 3492014 | 10/2022 |
| JP | 2005287762 | 10/2005 |
| JP | 2005315871 | 11/2005 |
| JP | 2006507078 | 3/2006 |
| JP | 2006126715 | 5/2006 |
| JP | 2007525858 | 9/2007 |
| JP | 2009537247 | 10/2009 |
| WO | 9625978 | 8/1996 |
| WO | 9719188 | 5/1997 |
| WO | 9801071 | 1/1998 |
| WO | 9902651 | 1/1999 |
| WO | 0018289 | 4/2000 |
| WO | 0025863 | 5/2000 |
| WO | 200025862 | 5/2000 |
| WO | 0180728 | 11/2001 |
| WO | 2004039265 | 5/2004 |
| WO | 2004071291 | 8/2004 |
| WO | 2004081522 | 9/2004 |
| WO | 2004091719 | 10/2004 |
| WO | 2004092713 | 10/2004 |
| WO | 2005074612 | 8/2005 |
| WO | 2006017169 | 2/2006 |
| WO | 2007110867 | 10/2007 |
| WO | 2007137037 | 11/2007 |
| WO | 2008076491 | 6/2008 |
| WO | 2009038996 | 3/2009 |
| WO | 2013016573 | 1/2013 |
| WO | 2015048514 | 4/2015 |
| WO | 2019023093 | 1/2019 |
| WO | 2019040635 | 2/2019 |

OTHER PUBLICATIONS

Renoe, B. W., McDonald, J. M., Ladenson, J. H. (1979). Influence of posture on free calcium and related variables. Clinical Chemistry, 25(10), 1766-1769. https://doi.org/10.1093/clinchem/25.10.1766 (Year: 1979).*

Statland, B. E., et al. (1974). Factors contributing to intra-individual variation of serum constituents: 4. effects of posture and tourniquet application on variation of serum constituents in healthy subjects. Clinical Chemistry, 20(12), 1513-1519. doi.org/10.1093/clinchem/20.12.1513 (Year: 1974).*

Bansal VK. Serum Inorganic Phosphorus. In: Walker HK, Hall WD, Hurst JW, editors. Clinical Methods: The History, Physical, and Laboratory Examinations. 3rd ed. Boston: Butterworths; 1990. Chapter 198. PMID: 21250152. (Year: 1990).*

Communication Pursuant to Article 94(3) EPC for European Patent Application No. 18174561.3 dated Jan. 27, 2020 (5 pages).

International Preliminary Report on Patentability for PCT Application No. PCT/US2018/043225 dated Feb. 6, 2020 (7 pages).

International Preliminary Report on Patentability for PCT Application No. PCT/US2018/047549 dated Mar. 5, 2020 (11 pages).

Response to Communication Pursuant to Rule 69 EPC for European Patent Application No. 18202201.2 filed Jan. 31, 2020 (22 pages).

Response to Communication Pursuant to Rule 69 EPC for European Patent Application No. 18209525.7 filed with the EPO Dec. 12, 2019 (33 pages).

Response to European Search Report for European Patent Application No. 18188253.1 filed Nov. 7, 2019 (14 pages).

Response to Extended European Search Report for European Patent Application No. 18207668.7 filed Nov. 29, 2019 (14 pages).

Bakker, Eric et al., "Carrier-Based Ion-Selective Electrodes and Bulk Optodes. 1. General Characteristics," Chem. Rev. 1997, 97, 3083-3132 (50 pages).

Benco, John S. et al., "Optical Sensors for Blood Analytes," The Spectrum, vol. 14, Issue 4, pp. 4-11, Winter 2001 (8 pages).

Bender, J. W. et al., "The Use of Biomedical Sensors to Monitor Capsule Formation Around Soft Tissue Implants," Annals of Plastic Surgery, vol. 56, No. 1, Jan. 2006, pp. 72-77 (6 pages).

Buhlmann, Philippe et al., "Carrier-Based Ion-Selective Electrodes and Bulk Optodes. 2. Ionophores for Potentiometric and Optical Sensors," Chem. Rev. 1998, 98, 1593-1687 (95 pages).

"Communication Pursuant to Article 94(3) EPC," for European Patent Application No. 07762189.4 dated Mar. 24, 2009 (3 pages).

"Communication pursuant to Article 94(3) EPC," for European Patent Application No. 07762189.4 dated Mar. 16, 2010 (3 pages).

Han, In S. et al., "Constant-Volume Hydrogel Osmometer: A New Device Concept for Miniature Biosensors," Biomacromolecules, 3 2002, pp. 1271-1275 (5 pages).

He, Huarui et al., "Enantioselective Optodes," Analytica Chimica Acta, 246, pp. 251-257, 1991 (7 pages).

"International Search Report and Written Opinion," for PCT Application No. PCT/US2018/043225 dated Nov. 16, 2018 (11 pages).

"International Search Report and Written Opinion," for PCT Application No. PCT/US2018/047549 dated Oct. 26, 2018 (15 pages).

Kuwana, Eddy et al., "Sensing of pH in Multiply Scattering Media with Fluorescence Lifetime," Advanced Biomedical and Clinical Diagnostic Systems, Proceedings of SPIE, vol. 4958, pp. 32-42, 2003 (11 pages).

Lehn, J. M. et al., "[2]-Cryptates: Stability and Selectivity of Alkali and Akaline-Earth Macrobicycle Complexes," Journal of the American Chemical Society, Nov. 12, 1975 pp. 6700-6707 (8 pages).

"Microminiature Device Monitors Vital Electrolytes and Metabolites," John Glenn Biomedical Engineering Consortium, May 2002 (2 pages).

"Microminiature Monitor for Vital Electrolyte and Metabolite Levels of Astronauts—Status Report," John Glenn Biomedical Engineering Consortium NASA Glenn Research Center at Lewis Field, Apr. 2003 (5 pages). NASA Glenn Research Center at Lewis Field.

"Partial European Search Report," for European Patent Application No. 18188253.1 dated Jan. 7, 2019 (11 pages).

"PCT International Search Report and Written Opinion," for International Application No. PCT/US2007/068954, dated Nov. 17, 2008 (12 pages).

"Response to Communication Pursuant to Article 94(3) EPC," for European Patent Application No. 07762189.4 filed with the EPO Jul. 27, 2009 (8 pages).

Tohda, Koji et al., "A Microscopic, Continuous, Optical Monitor for Interstitial Electrolytes and Glucose," Chemphyschem 2003, pp. 155-160 (6 pages).

(56) References Cited

OTHER PUBLICATIONS

Tohda, Koji et al., "Micro-miniature Autonomous Optical Sensor Array for Monitoring Ions and Metabolites 1: Design, Fabrication, and Data Analysis," Analytical Sciences, Mar. 2006, vol. 22 pp. 383-388 (6 pages).
Tsai, HC et al., "Simultaneous Determination of Renal Clinical Analytes in Serum using Hydrolase- and Oxidase-Encapsulated Optical Array Biosensors," Analytical Biochemistry 334 (2004) 183-192 (10 pages).
Voskerician, Gabriela et al., "Biocompatibility and Biofouling of MEMs Drug Delivery Devices," Biomaterials 24 (2003) 1959-1967 (9 pages).
Anderson, J. M. et al., "Monocyte, Macrophage and foreign body giant cell interactions with molecularly engineered surfaces," Journal of Materials Science: Materials in Medicing 10 (1999) 579-588 (10 pages).
Anderson, James M. "Biological Responses to Materials," Annu. Rev. Mater. Res. 2001. 31:81-110 (30 pages).
Anderson, James M. et al., "Foreign Body Reaction to Biomaterials," Semin. Immunol. Apr. 2008; 20(2): 86-100 (27 pages).
Bridges, Amanda W. et al., "Anti-Inflammatory Polymeric Coatings for Implantable Biomaterials and Devices," Journal of Diabetes Science and Technology 2008;2(6):984-994 (11 pages).
"Extended European Search Report," for European Patent Application No. 18174561.3 dated Aug. 28, 2018 (9 pages).
File History for European Patent Application No. 08799344.0 downloaded Sep. 11, 2018 (154 pages).
File History for U.S. Appl. No. 11/856,850 downloaded Sep. 11, 2018 (456 pages).
File History for U.S. Appl. No. 12/391,761 downloaded Sep. 11, 2018 (286 pages).
"First Examination Report," for Australian Patent Application No. 2008302499 dated Feb. 8, 2011 (1 page)., 1 Pg.
He, Wei et al., "A Novel Anti-inflammatory Surface for Neural Electrodes," Adv. Mater. 2007, 19, 3529-3533 (5 pages).
Helton, Kristen L. et al., "Biomechanics of the Sensor-Tissue Interface-Effects of Motion, Pressure, and Design on Sensor Performance and the Foreign Body Response—Part I: Theoretical Framework," Journal of Diabetes Science and Technology 2011;5(3):632-646 (15 pages).
"International Preliminary Report on Patentability," for PCT Application No. PCT/US2008/075673 dated Mar. 24, 2010 (6 pages).
"Japanese Office Action," for Japanese Application No. 2010-524940, corresponding to U.S. Appl. No. 11/856,850, dated Nov. 22, 2011, (pp. 31) Including English translation., 31.
Koh, Ahyeon et al., "Glucose Sensor Membranes for Mitigating the Foreign Body Response," Journal of Diabetes Science and Technology 2011;5(5):1052-1059 (8 pages).
Koronczi, et al., "Development of a submicron optochemical potassium sensor with enhanced stability due to internal reference," Sensors and Actuators B, 51:188-195 (1998).
Lima-Oliveira, Gabriel et al., "Patient Posture for Blood Collection by Venipuncture: Recall for Standardization After 28 Years," Brazilian Journal of Hematology and Hemotherapy 2017 <http://dx.doi.org/10.1016/j.bjhh.2017.01.004> (6 pages).
Messler, "The Joining of Materials," Nov. 2004, 389-446.
"Notice of allowance Received," Citation for Japanese Application No. 2010-524940, corresponding to U.S. Appl. No. 11/856,850, dated Jul. 3, 2012 (3 pages).
Novak, Matthew T. et al., "Modeling the relative impact of capsular tissue effects on implanted glucose sensor time lag and signal attenuation," Anal. Bioanal. Chem. Oct. 2010; 398(4):1695-1705 (22 pages).
Padmanabhan, Jagnnath et al., "Nanomaterials, Inflammation and Tissue Engineering," Wiley Interdiscip Rev Nanomed Nanobiotechnol. May 2015; 7(3):355-370 (23 pages).
"PCT International Search Report and Written Opinion from International Application No. PCT /US2008/075673, dated Nov. 28, 2008, pp. 1-13,".
Roger, Yvonne et al., "Grid-like surface structures in thermoplastic polyurethane induce anti-inflammatory and anti-fibrotic processes in bone marrow-derive dmesenchymal stem cells," Abstract Only Colloids and Surfaces B: Biointerfaces vol. 148, Dec. 2016, pp. 104-115 (4 pages).
Seelig, Mildred S. "Electrographic Patterns of Magnesium Depletion Appearing in Alcoholic Heart Disease," Annals of the New York Academy of Sciences, vol. 162, Article 2, 1969, pp. 906-917 (13 pages).
Sharkawy, A. A. et al., "Engineering the tissue which encapsulates subcutaneous implants. I. Diffusion properties," Department of Biomedical Engineering, NSF Center for EmergingCardiovascular Technology, Duke University, Durham, North Carolina 1996 (12 pages).
Shirreffs, S. M. "The Effect of Posture Change on Blood Volume, Serum Potassium, and Whole Body Electrical Impedance," Eur. J. Appl. Physiol. (1994)69:461-463 (3 pages).
"Upconverting nanoparticles," Wikipeda.com accessed Jun. 12, 2017 (13 pages).
Weisberg, Lawrence S. "Management of Severe Hyperkalemia," Crit Care Med 2008 vol. 36, No. 12 (6 pages).
Extended European Search Report for European Patent Application No. 18188253.1 dated Apr. 9, 2019 (10 pages).
Extended European Search Report for European Patent Application No. 18207668.7 dated Apr. 3, 2019 (7 pages).
Extended European Search Report for European Patent Application No. 18209525.7 dated Feb. 27, 2019 (12 pages).
Extended European Search Report for European Patent Application No. 18202201.2 dated Jun. 28, 2019 (9 pages).
Response to Communication Pursuant to Rule 69 EPC for European Patent Application No. 18174561.3 filed Jun. 3, 2019 (21 pages).
Non-Final Office Action for U.S. Appl. No. 15/992,823 dated May 5, 2020 (51 pages).
Non-Final Office Action for U.S. Appl. No. 16/038,737 dated Jun. 22, 2020 (46 pages).
Non-Final Office Action for U.S. Appl. No. 16/136,773 dated Jun. 1, 2020 (43 pages).
Non-Final Office Action for U.S. Appl. No. 16/136,875 dated May 27, 2020 (43 pages).
Communication Pursuant to Article 94(3) EPC for European Patent Application No. 18207668.7 dated Aug. 4, 2020 (5 pages).
Final Office Action for U.S. Appl. No. 15/992,823 dated Aug. 13, 2020 (18 pages).
Final Office Action for U.S. Appl. No. 16/136,875 dated Aug. 21, 2020 (10 pages).
Non-Final Office Action for U.S. Appl. No. 16/106,623 dated Oct. 9, 2020 (60 pages).
Non-Final Office Action dated May 27, 2020 for U.S. Appl. No. 16/136,875, 43 pages.
Response to Communication Pursuant to Article 94(3) EPC, for European Patent Application No. 18174561.3 filed Jul. 27, 2020 (11 pages).
Response to Non-Final Rejection dated Jun. 1, 2020 for U.S. Appl. No. 16/136,773, submitted via EFS-Web on Aug. 20, 2020, 10 pages.
Response to Non-Final Rejection dated Jun. 22, 2020 for U.S. Appl. No. 16/038,737, submitted via EFS-Web on Aug. 4, 2020, 10 pages.
Response to Non-Final Rejection dated May 27, 2020 for U.S. Appl. No. 16/136,875, submitted via EFS-Web on Jul. 22, 2020, 11 pages.
Response to Non-Final Rejection dated May 5, 2020 for U.S. Appl. No. 15/992,823, submitted via EFS-Web on Jul. 7, 2020, 10 pages.
"Non-Final Office Action," for U.S. Appl. No. 16/038,737 dated Mar. 24, 2021 (14 pages).
"Notice of Allowance," for U.S. Appl. No. 15/992,823 dated Jun. 10, 2021 (16 pages).
"Notice of Allowance," for U.S. Appl. No. 16/136,875 dated Apr. 15, 2021 (13 pages).
"Response to Communication Pursuant to Article 94(3) EPC," for European Patent Application No. 18209525.7 filed Apr. 15, 2021 (10 pages).
"Response to Non-Final Rejection," dated Dec. 23, 2020 for U.S. Appl. No. 15/992,823, submitted via EFS-Web on Mar. 23, 2021, 9 pages.

(56) References Cited

OTHER PUBLICATIONS

"Response to Non-Final Rejection," dated Jan. 25, 2021 for U.S. Appl. No. 16/136,875, submitted via EFS-Web on Mar. 17, 2021, 12 pages.
"Response to Non-Final Rejection," dated Mar. 24, 2021 for U.S. Appl. No. 16/038,737, submitted via EFS-Web on Jun. 18, 2021, 11 pages.
Communication Pursuant to Article 94(3) EPC for European Patent Application No. 18207668.7 dated Jan. 13, 2021 (4 pages).
Communication Pursuant to Article 94(3) EPC for European Patent Application No. 18209525.7 dated Dec. 8, 2020 (5 pages).
Final Office Action for U.S. Appl. No. 16/038,737 dated Nov. 2, 2020 (15 pages).
Non-Final Office Action for U.S. Appl. No. 15/992,823 dated Dec. 23, 2020 (18 pages).
Non-Final Office Action for U.S. Appl. No. 16/136,875 dated Jan. 25, 2021 (12 pages).
Notice of Allowance for U.S. Appl. No. 16/136,773 dated Nov. 18, 2020 (17 pages).
Response to Communication Pursuant to Article 94(3) EPC for European Patent Application No. 18207668.7 filed Dec. 11, 2020 (65 pages).
Response to Communication Pursuant to Rules 161(1) and 162 EPC for European Patent Application No. 18773017.1 filed Sep. 30, 2020 (13 pages).
Response to Final Rejection dated Aug. 21, 2020 and Advisory Action dated Oct. 19, 2020 for U.S. Appl. No. 16/136,875, submitted via EFS-Web on Nov. 20, 2020, 14 pages.
Response to Final Rejection dated Nov. 2, 2020 for U.S. Appl. No. 16/038,737, submitted via EFS-Web on Feb. 2, 2021, 9 pages.
Response to Non-Final Rejection dated Oct. 9, 2020 for U.S. Appl. No. 16/106,623, submitted via EFS-Web on Jan. 8, 2021, 21 pages.
"Final Office Action," for U.S. Appl. No. 16/038,737 dated Sep. 7, 2021 (12 pages).
"Non-Final Office Action," for U.S. Appl. No. 16/106,623 dated Aug. 25, 2021 (31 pages).
"Non-Final Office Action," for U.S. Appl. No. 16/130,638 dated Aug. 23, 2021 (67 pages).
"Response to Communication Pursuant to Article 94(3) EPC," for European Patent Application No. 18207668.7 filed May 21, 2021 (32 pages).
"First Office Action," for Chinese Patent Application No. 201710681567.3 dated Mar. 18, 2022 (16 pages) with English Translation.
"International Search Report and Written Opinion," for PCT Application No. PCT/US2021/056602 dated Feb. 9, 2022 (12 pages).
"Invitation to Pay Additional Fees," for PCT Application No. PCT/US2021/056590 dated Mar. 9, 2022 (9 pages).
"Non-Final Office Action," for U.S. Appl. No. 16/038,737 dated Mar. 3, 2022 (17 pages).
"Response to Final Rejection," dated Jan. 26, 2022 and the Advisory Action dated Apr. 18, 2022 for U.S. Appl. No. 16/130,638, submitted via EFS-Web on Apr. 26, 2022, 7 pages.
"Response to Final Rejection," dated Jan. 26, 2022 for U.S. Appl. No. 16/130,638, submitted via EFS-Web on Mar. 24, 2022, 8 pages.
"Response to Final Rejection," dated Dec. 2, 2021 and the Advisory Action dated Apr. 5, 2022 for U.S. Appl. No. 16/106,623, submitted via EFS-Web on May 2, 2022, 14 pages.
"Response to Final Rejection," dated Dec. 2, 2021 for U.S. Appl. No. 16/106,623, submitted via EFS-Web on Feb. 24, 2022, 14 pages.
"Response to Non-Final Rejection," dated Mar. 3, 2022 for U.S. Appl. No. 16/038,737, submitted via EFS-Web on May 4, 2022, 10 pages.
"Final Office Action," for U.S. Appl. No. 16/106,623 dated Dec. 2, 2021 (25 pages).
"Final Office Action," for U.S. Appl. No. 16/130,638 dated Jan. 26, 2022 (16 pages).
"First Office Action," for Chinese Patent Application No. 201710400287.0 dated Dec. 23, 2021 (37 pages) with English Translation.
"Response to Final Rejection," dated Sep. 7, 2021 for U.S. Appl. No. 16/038,737, submitted via EFS-Web on Nov. 30, 2021, 10 pages.
"First Office Action," for Chinese Patent Application No. 201710730979.1 dated Apr. 11, 2022 (23 pages) with English Translation.
"International Search Report and Written Opinion," for PCT Application No. PCT/US2021/056590 dated May 3, 2022 (14 pages).
"Non-Final Office Action," for U.S. Appl. No. 16/130,638 dated May 6, 2022 (13 pages).
"Notice of Allowance," for U.S. Appl. No. 16/038,737 dated May 18, 2022 (13 pages).
"Non-Final Office Action," for U.S. Appl. No. 16/106,623 dated Jun. 24, 2022 (19 pages).
"Response to Non-Final Rejection," dated May 6, 2022 for U.S. Appl. No. 16/130,638, submitted via EFS-Web on Aug. 5, 2022, 7 pages.
"Communication Pursuant to Article 94(3) EPC," for European Patent Application No. 18202201.2 dated Nov. 9, 2022 (6 pages).
"Final Office Action," for U.S. Appl. No. 16/130,638 dated Nov. 2, 2022 (12 pages).
"First Office Action," for Chinese Patent Application No. 201711052948.1 dated Oct. 28, 2022 (21 pages) with English Translation.
"Response to Non-Final Rejection," dated Jun. 24, 2022 for U.S. Appl. No. 16/106,623, submitted via EFS-Web on Sep. 22, 2022, 7 pages.
"First Office Action," for Chinese Patent Application No. 201711249985.1 dated Feb. 27, 2023 (11 pages), with English translation.
"International Preliminary Report on Patentability," for PCT Application No. PCT/US2021/056590 dated May 11, 2023 (9 pages).
"International Preliminary Report on Patentability," for PCT Application No. PCT/US2021/056602 dated May 11, 2023 (8 pages).
"Non-Final Office Action," for U.S. Appl. No. 16/130,638 dated May 18, 2023 (13 pages).
"Non-Final Office Action," for U.S. Appl. No. 17/510,802 dated Jun. 1, 2023 (52 pages).
"Response to Communication Pursuant to Article 94(3) EPC," for European Patent Application No. 18202201.2 filed Mar. 17, 2023 (33 pages).
"Response to Final Rejection," dated Nov. 2, 2022 and the Advisory Action dated Mar. 17, 2023 for U.S. Appl. No. 16/130,638, submitted via EFS-Web on Apr. 3, 2023, 9 pages.
"Response to Final Rejection," dated Nov. 2, 2022 for U.S. Appl. No. 16/130,638, submitted via EFS-Web on Feb. 1, 2023, 8 pages.
"Second Office Action," for Chinese Patent Application No. 201711052948.1 dated May 17, 2023 (11 pages) with English translation.
"Final Office Action," for U.S. Appl. No. 17/510,802 dated Oct. 5, 2023 (13 pages).
"Non-Final Office Action," for U.S. Appl. No. 17/510,903 dated Aug. 16, 2023 (55 pages).
"Response to Non-Final Rejection," dated Jun. 1, 2023, for U.S. Appl. No. 17/510,802, submitted via EFS-Web on Aug. 31, 2023, 9 pages.
"Response to Non-Final Rejection," dated May 18, 2023, for U.S. Appl. No. 16/130,638, submitted via EFS-Web on Aug. 17, 2023, 12 pages.
"Response to Non-Final Rejection," mailed on Aug. 23, 2021 for U.S. Appl. No. 16/130,638, submitted via EFS-Web on Nov. 1, 2021, 9 pages.
"Response to Non-Final Rejection," mailed on Aug. 25, 2021 for U.S. Appl. No. 16/106,623, submitted via EFS-Web on Oct. 27, 2021, 14 pages.

\* cited by examiner

SYSTEMS AND METHODS FOR DISAMBIGUATION OF POSTURE

This application claims the benefit of U.S. Provisional Application No. 62/537,047, filed Jul. 26, 2017, the content of which is herein incorporated by reference in its entirety.

FIELD

Embodiments herein relate to medical device systems, medical devices, including accelerometers and chemical sensors, and methods of using the same.

BACKGROUND

The posture of a patient can be a significant factor to consider for various clinical purposes including assessing the condition of a patient, providing treatment to a patient, etc.

Many different types of sensors can be included with modern medical devices. Accelerometers are one type of sensor included with some modern medical devices. Accelerometer data can reflect movement of the patient as well as the orientation of the sensor within the patient with respect to gravity.

Chemical sensors are another type of sensor included with some modern medical devices. Chemical sensors can measure and report concentrations of physiological analytes (e.g., potassium, creatinine, etc.).

SUMMARY

Embodiments include medical device systems, medical devices, including accelerometers and chemical sensors, and methods of using the same to determine the posture of a patient.

In a first aspect, a medical device system is included. The medical device system can have an accelerometer configured to generate a signal reflecting a position of a patient, a chemical sensor configured to generate a signal reflecting physiological analyte data of the patient and a controller in electrical communication with the accelerometer and the chemical sensor. The controller can be configured to determine a posture of the patient using the signal generated by the accelerometer and the signal generated by the chemical sensor.

In a second aspect, in addition to or in place of other aspects herein, the controller can be configured to differentiate between a sitting posture and a standing posture of a patient.

In a third aspect, in addition to or in place of other aspects herein, the controller can be further configured to make a preliminary posture determination using the signal generated by the accelerometer and make a final posture determination using the signal generated by the chemical sensor.

In a fourth aspect, in addition to or in place of other aspects herein, at least a portion of the medical device system is implantable.

In a fifth aspect, in addition to or in place of other aspects herein, the chemical sensor is configured to measure a component selected from the group consisting of a cellular interstitial component, a blood component and a breath component.

In a sixth aspect, in addition to or in place of other aspects herein, the accelerometer is a multi-axis accelerometer.

In a seventh aspect, in addition to or in place of other aspects herein, the chemical sensor is configured to measure one or more physiological analytes including one or more selected from the group consisting of an electrolyte, a protein, a sugar, a hormone, a peptide, an amino acid, or a metabolic product.

In an eighth aspect, in addition to or in place of other aspects herein, an electrolyte measured by the chemical sensor is one or more of potassium, calcium, sodium, magnesium, hydrogen phosphate, chloride, or bicarbonate.

In a ninth aspect, in addition to or in place of other aspects herein, the system can further include a therapy unit configured to control a therapy delivered to a patient; and wherein the controller is further configured to modify a therapy delivered by the therapy unit based on the posture determination of a patient.

In a tenth aspect, in addition to or in place of other aspects herein, the therapy unit can deliver one or more of an electrical stimulation therapy or a pharmaceutical therapy.

In an eleventh aspect, in addition to or in place of other aspects herein, the system can further include a visual display configured to show the posture determination of a patient.

In a twelfth aspect, in addition to or in place of other aspects herein, the visual display can further show the posture determination of a patient as a time trend.

In a thirteenth aspect, in addition to or in place of other aspects herein, the visual display can further be configured to show the posture determination of a patient along with at least one of a physiological parameter, a therapy dose, or a time of day.

In a fourteenth aspect, in addition to or in place of other aspects herein, the at least one physiological parameter selected from the group consisting of a cardiac parameter, a pulmonary parameter, a renal parameter, and a nerve parameter.

In a fifteenth aspect, in addition to or in place of other aspects herein, the physiological parameter is displayed as a function of the posture determination of a patient.

In a sixteenth aspect, in addition to or in place of other aspects herein, a physiological parameter is collected, aggregated, and displayed by the system only for time periods when the patient is in a specified set of determined postures.

In a seventeenth aspect, in addition to or in place of other aspects herein, the system further including one or more additional medical devices, wherein the medical devices are communicatively coupled.

In an eighteenth aspect, a method of operating a medical device system is included. The method can include measuring position data using an accelerometer; making a preliminary posture determination of a patient using data measured by an accelerometer; measuring chemical data using a chemical sensor; and making a final posture determination of a patient using data measured by an accelerometer and data measured by a chemical sensor.

In a nineteenth aspect, in addition to or in place of other aspects herein, a method of operating a medical device system is included. The method can include measuring position data using an accelerometer; making a preliminary posture determination of a patient using data measured by an accelerometer. According to the method, if the preliminary posture determination does not indicate a recumbent posture, then the method can include measuring chemical data using a chemical sensor and making a final posture determination of a patient using data measured by an accelerometer and data measured by a chemical sensor.

In a twentieth aspect, in addition to or in place of other aspects herein, the method can include activating the chemical sensor if the preliminary posture determination does not indicate a recumbent posture.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

Figure 1:
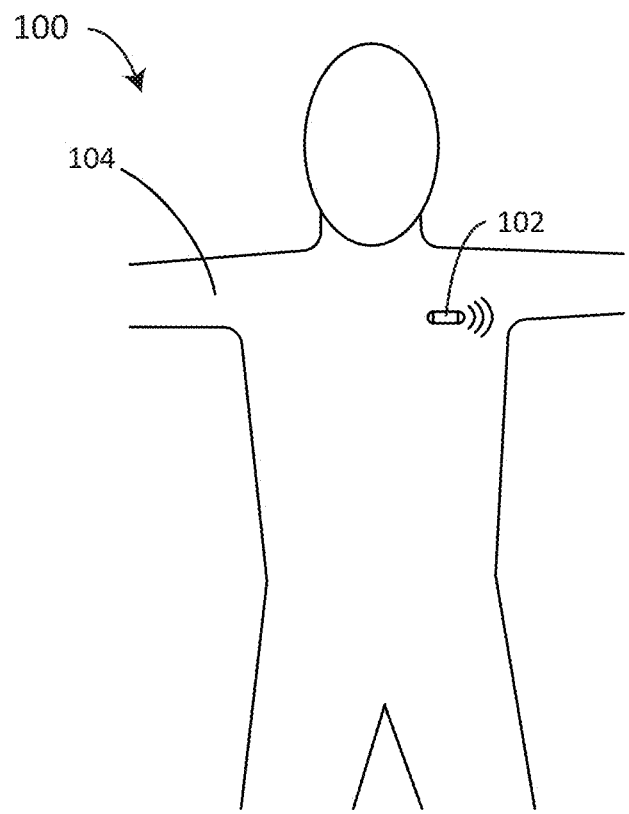
FIG. 1 is a schematic view of a medical device system implanted within a patient in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

As referenced above, the posture of a patient (including, but not limited to, standing, sitting or lying down) can be a significant factor to consider for various clinical purposes including assessing the condition of a patient, providing treatment to a patient, etc.

Further, specifically differentiating between a sitting and standing posture is clinically relevant for a number of reasons. There are a many hemodynamic factors that affect blood flow and blood distribution within the body when comparing sitting versus standing postures in a diseased and healthy individual. For example, while standing, more blood is distributed to the legs where in a healthy individual it will return to the heart with the assistance of contractions of the muscles within the skeletal-muscle pump. Yet, in some diseased states, such as heart failure and orthostatic intolerance, the skeletal-muscle pump is not enough to assist in circulating the blood back to the heart, and as a result a patient can experience a worsening of the underlying symptoms (e.g., changes in heart rate, syncope, edema, etc.) of disease. As such, optimal therapy for a diseased state may be dependent on whether an affected individual is sitting or standing.

Accelerometer data can be used to assess aspects of the position of a patient. For example, accelerometer data can be used to differentiate between an upright (or vertically oriented) and horizontally oriented position of the patient. As used herein, reference to the terms "lying down" or "recumbent" shall be inclusive of prone (lying face-down), supine (laying face-up), right lateral recumbent, and left lateral recumbent postures. In some embodiments, recumbent can include where the patient is not completely horizontal but up to 10, 15, 20, 25, or 30 degrees elevated with respect to horizontal. Further, accelerometer data can typically be used to differentiate between a prone and a supine posture. However, accelerometer data by itself, when the accelerometer is disposed on or within the torso of the patient, is typically insufficient to differentiate between a sitting posture and a standing posture because the position of the torso can be very similar whether the patient is sitting or standing (e.g., the torso can be vertically oriented whether sitting or standing).

Chemical sensors are another type of sensors included with some modern medical devices. Chemical sensors can measure and report concentrations of physiological analytes (e.g., potassium, creatinine, etc.). Interestingly, serum concentrations of physiological analytes, such as potassium and other blood constituents, can vary based on posture.

Applicants have discovered that accelerometer data and chemical sensor data can be combined and/or monitored synchronously to differentiate between a sitting and standing posture. In some embodiments herein, both accelerometer data and chemical sensor data can be utilized to determine whether a patient is in a standing posture or sitting (or seated) posture, and, in some cases, therapy can be tailored accordingly.

Referring now to FIG. 1, a schematic view is shown of a medical device system 100 in accordance with the embodiments. In some embodiments, medical device system 100 can include an implantable medical device 102, as shown in FIG. 1. In other embodiments, at least a portion of the medical device system can be implantable. In some embodiments, the implantable medical device 102 can include an implantable loop recorder, implantable monitor device, or the like. In some embodiments, implantable medical device 102 can be implanted within the body of a patient 104. Various implant sites can be used including the upper torso, the abdominal area, and the like. In some embodiments, the medical device system can include one or more additional medical devices that are communicatively coupled to one another.

Figure 2:
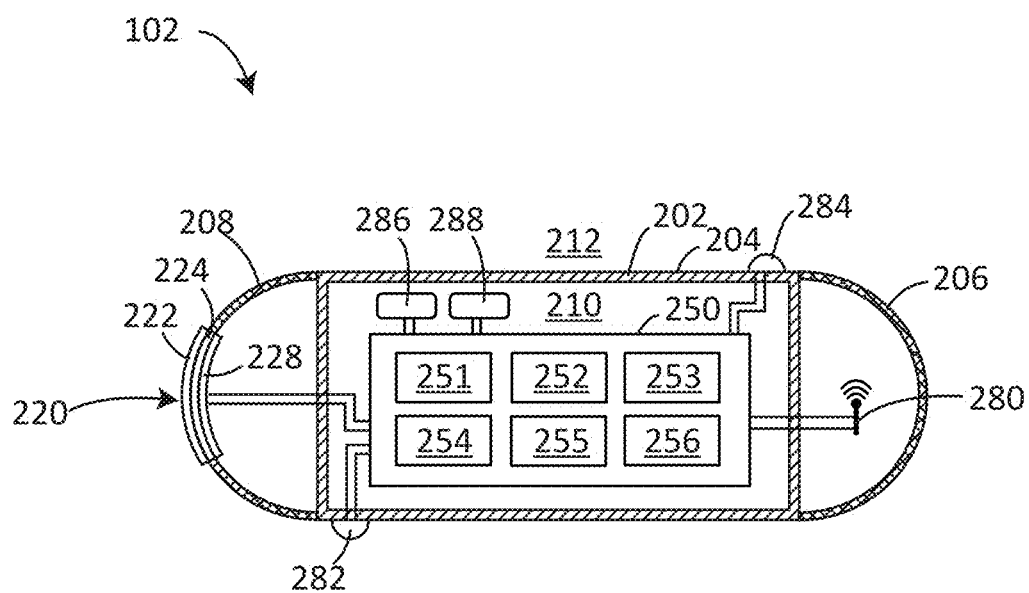
FIG. 2 is a schematic cross-sectional view of the implantable medical device shown in FIG. 1, in accordance with various embodiments herein.

Referring now to FIG. 2, a schematic cross-sectional view of the implantable medical device 102 is shown in accordance with various embodiments herein. The implantable device 102 includes a housing 202. The housing 202 can include various materials such as metals, polymers, ceramics, and the like. In some embodiments, the housing 202 can be a single integrated unit. In other embodiments, the housing 202 can include a main segment 204 along with appendage segments 206 and 208. In one embodiment, the housing 202, or one or more portions thereof, can be formed of titanium. In some embodiments, one or more segments of the housing 202 can be hermetically sealed. In some embodiments, the main segment 204 can be formed of a metal and the appendage segments 206 and 208 can be formed from a polymeric material.

The housing 202 defines an interior volume 210 that in some embodiments is hermetically sealed off from the area 212 outside of the implantable medical device. The implantable medical device 102 can include circuitry 250. The circuitry 250 can include various components, including, but not limited to a controller 251, an accelerometer 252, a microprocessor 253, therapy unit circuitry 254, recorder circuitry 255, and sensor interface circuitry 256. Other examples of components suitable for use in the medical device systems embodied herein can include telemetry circuitry, memory circuitry (e.g., such as random access memory (RAM) and/or read only memory (ROM)), power supply circuitry (which can include, but not be limited to, one or more batteries, a capacitor, a power interface circuit, etc.), normalization circuitry, control circuitry, electrical field sensor and stimulation circuitry, display circuitry, and the like.

In some embodiments, one or more components can be integrated into the implantable medical device and in other embodiments one or more components can be separate. In some embodiments recorder circuitry can record the data produced by the chemical sensor and/or the accelerometer and record time stamps regarding the same. In some embodiments, the circuitry can be hardwired to execute various functions while in other embodiments, the circuitry can be implemented as instructions executing on a controller, a microprocessor, other computation device, application specific integrated circuit (ASIC), or the like.

Implantable medical device 102 can include an accelerometer 252. In some embodiments, accelerometer 252 can be a multi-axis accelerometer, such as a 3-axis accelerometer. Accelerometer 252 can be configured to measure position data of a patient. In some embodiments, accelerometer 252 can be configured to assess a preliminary posture of a patient at a given time point. In some embodiments, accelerometer 252 can be configured to assess, in combination with chemical sensor data, a final posture of a patient at a given time point. In some embodiments, accelerometer 252 can be configured to measure multiple position and/or posture variations of a patient over a given time period.

In some embodiments, the implantable medical device 102 can include a chemical sensor 220. However, in other embodiments, the chemical sensor may be external such as with in vitro testing or disposed in a separate implanted device that can be in communication (wired or wireless) with the implantable medical device 102. In the embodiment shown in FIG. 2, the chemical sensor is an optical chemical sensor. However, in other embodiments the chemical sensor can be a potentiometric chemical sensor. The chemical sensor 220 can specifically include at least one chemical sensing element 222, an optical window 224, and an electro-optical module 228. The electro-optical module 228 can be in electrical communication with the circuitry 250 within the interior volume 210. In some embodiments, the control circuitry 250 is configured to selectively activate the chemical sensor 220. The chemical sensor 220 can be configured to be chronically implanted or it can be configured to be temporarily implanted. In some embodiments, the chemical sensor 220 can be configured to measure a cellular interstitial component, a blood component, or a breath component, or any analytes thereof. In some embodiments the blood component can include blood constituents or analytes thereof, such as red blood cells; white blood cells including at least neutrophils, eosinophils, and basophils; platelets; hemoglobin; and the like.

The chemical sensor 220 can include an electro-optical module 228 coupled to the optical window 224. The electro-optical module 228 can specifically include one or more optical excitation assemblies. Each optical excitation assembly can include various light sources such as light-emitting diodes (LEDs), vertical-cavity surface-emitting lasers (VCSELs), electroluminescent (EL) devices or the like. The electro-optical module 228 can also include one or more optical detection assemblies. Each optical detection assembly can include one or more photodiodes, avalanche photodiodes, a photodiode array, a photo transistor, a multi-element photo sensor, a complementary metal oxide semiconductor (CMOS) photo sensor, or the like.

The chemical sensing element 222 can be disposed on the optical window 224. The chemical sensing element 222 can be configured to detect a physiological analyte by exhibiting an optically detectable response to the physiological analyte. Specific examples of physiological analytes are discussed in greater detail below. In operation, physiological analytes of interest from the in vivo environment can diffuse into the chemical sensing element 222 causing a detectable change in the optical properties of the chemical sensing element 222. Light can be generated by the electro-optical module 228 and can pass through the optical window 224 and into the chemical sensing element 222. Light can then either be preferentially reflected from or re-emitted by the chemical sensing element 222 proportional to the sensed physiological analyte, and pass back through the optical window 224 before being received by the electro-optical module 228. Data regarding the specific physiological analyte of interest can be recorded by recorder circuitry 255 for use during posture analysis at a later time.

In some embodiments the chemical sensing element 222 can be located in a fluid such as blood, interstitial fluid, urine, lymph or chyle, and the sensing element 222 can sense physiological analytes in a fluid. In other embodiments, the chemical sensing element 222 can be located in a solid tissue such as cardiac or skeletal muscle, fat, bone, bone marrow, organ tissues (e.g. kidney, liver, brain, lung, etc.), and the sensing element 222 can sense physiological analytes in a solid tissue.

The implantable medical device 102 can include a controller 251. In some embodiments, the controller 251 can be configured to use position data measured by the accelerometer and physiological analyte data measured by the chemical sensor to make a posture determination of a patient. Controller 251 can be configured to differentiate between a sitting posture and a standing posture. In some embodiments, controller 251 can determine a preliminary posture of a patient using position data measured by the accelerometer 252. In some embodiments the preliminary posture can be either standing/sitting or lying down. In some embodiments, controller 251 can be configured to determine a final posture of a patient using position data measured by the accelerometer in conjunction with physiological analyte data measured by the chemical sensor. In some embodiments, the final posture can be selected from the group consisting of standing posture, sitting posture, and lying down (or recumbent) posture. In some embodiments, controller 251 can be configured to direct a therapy unit to deliver a therapy to a patient. In some embodiments, controller 251 can be configured to modify a therapy delivered to a patient based on the posture determination of a patient. In some embodiments, the controller is configured to modify an electrical stimulation therapy or a pharmaceutical therapy.

The implantable medical device 102 can include additional components, for example, a therapy unit 254. The therapy unit 254 can be configured to deliver a therapy to a patient and/or control or influence the delivery of a therapy provided by another device. In some embodiments, the therapy unit can be configured to provide optimum therapy to a patient depending on if they are in a standing or sitting posture. Examples of therapies include, but are not limited to pacing schemes such as rate-adaptive pacing, cardiac-resynchronization therapy (CRT), neurostimulation therapy, administration of therapeutic agents, and the like. In some embodiments, the therapy unit 254 can be a pharmaceutical therapy unit. In some embodiments, the therapy unit 254 can include both an electrical therapy unit and a pharmaceutical therapy unit. In some embodiments, the therapy unit 254 can be directed by the controller 251 to deliver a therapy and/or a modified therapy based on the posture determination of a patient.

An exemplary electrical stimulation therapy unit can include an electrical field sensor that is configured to generate a signal corresponding to cardiac electric fields. The electrical field sensor can include a first electrode 282 and a second electrode 284. In some embodiments, the housing 202 itself or one or more portions thereof can serve as an electrode. The electrodes can be in communication with the electrical field sensor. The electrical field sensor can include a circuit in order to measure the electrical potential difference (voltage) between the first electrode 282 and the second electrode 284. The implantable medical device 102 can also include an antenna 280, to allow for unidirectional or bidirectional wireless data communication within the medical device system 100.

Figure 3:
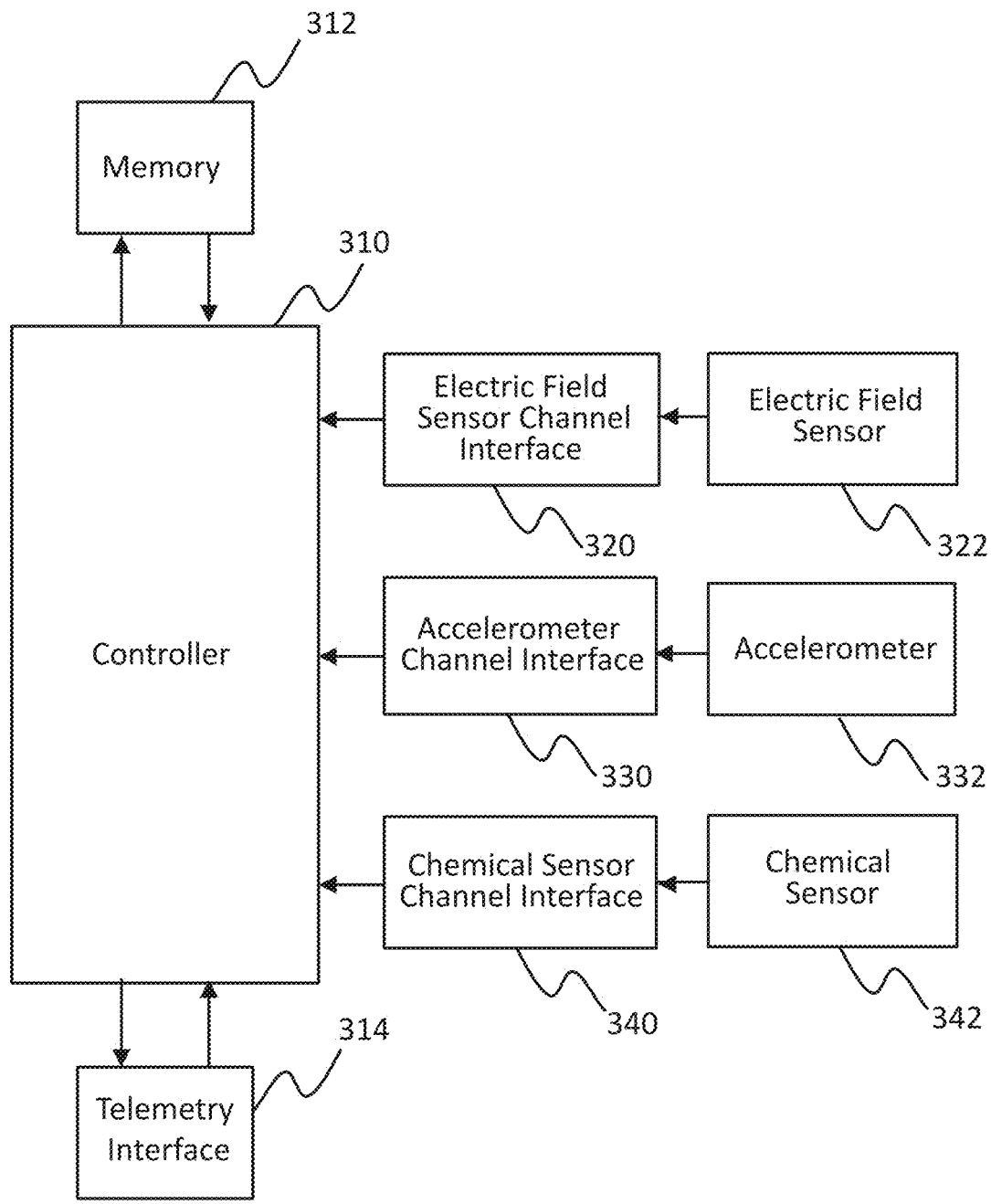
FIG. 3 is a schematic diagram of components of an implantable medical device in accordance with various embodiments herein.

Elements of some embodiments of a medical device system are shown in FIG. 3 in accordance with the embodiments herein. However, it will be appreciated that some embodiments can include additional elements beyond those shown in FIG. 3. In addition, some embodiments may lack some elements shown in FIG. 3. The medical device system, as embodied herein, can gather information through one or more sensing channels 322, 332, and 342. A controller 310 can communicate with a memory 312 via a bidirectional data bus. The memory 312 can include read only memory (ROM) or random access memory (RAM) for program storage and RAM for data storage.

In some embodiments, a medical device can include one or more electric field sensors 322 (i.e., electrodes) and an electric field sensor channel interface 320 that can communicate with a port of controller 310. The medical device can also include an accelerometer 332 and an accelerometer channel interface 330 that can communicate with a port of controller 310. The medical device can also include one or more chemical sensors 342 and a chemical sensor channel interface 340 that can communicate with a port of controller 310. The channel interfaces 320, 330 and 340 can include various components such as analog-to-digital converters for digitizing signal inputs, sensing amplifiers, registers that can be written to by the control circuitry in order to adjust the gain and threshold values for the sensing amplifiers, and the like. A telemetry interface 314 is also provided for communicating with external devices such as a programmer, a home-based unit, and/or a mobile unit (e.g. a cellular phone, laptop computer, etc.).

In some embodiments, the medical device can also include additional posture sensors, activity sensors, acoustic sensors, or respiration sensors integral to the medical device.

In some embodiments, the medical device can also include additional posture, activity, or respiration sensors that are separate from medical device. In various embodiments one or more of the posture sensors, activity sensors, or respiration sensors can be within another implanted medical device communicatively coupled to the medical device via telemetry interface 314. In various embodiments one or more of the additional posture sensors, activity sensors, or respiration sensors can be external to the body and are coupled to medical device via telemetry interface 314. Additional aspects of posture sensors and processing data from the same can be found in U.S. Pat. No. 7,471,290 and U.S. Publ. Pat. Appl. Nos. 2007/0118056; 2008/0082001; and 2009/0312973 the content of which related to posture sensors and processing data from the same is incorporated herein by reference.

Figure 4:
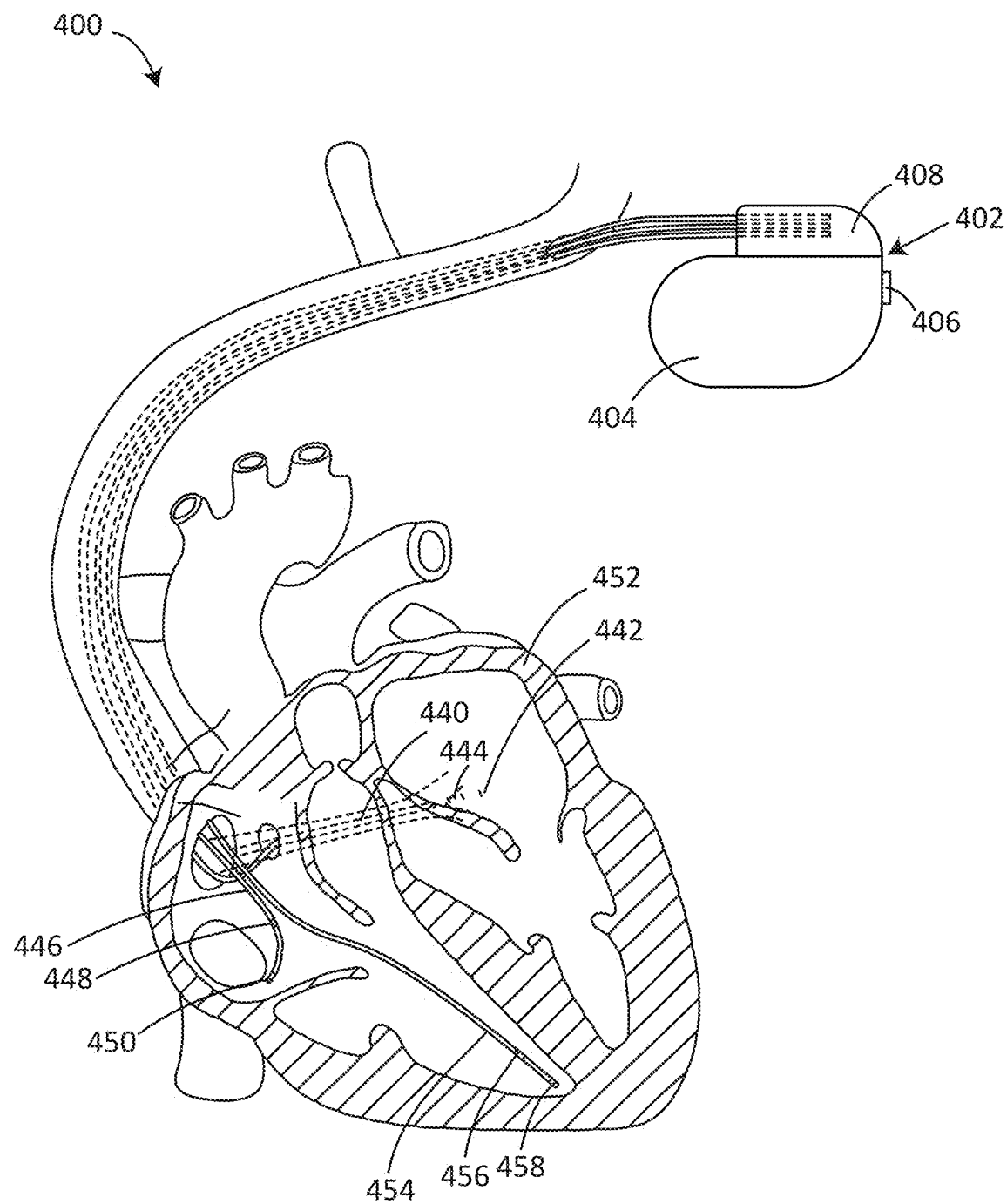
FIG. 4 is a schematic view of a medical device system in accordance with various embodiments herein.

Referring now to FIG. 4, a schematic view is shown of a medical device system 400 in accordance with the embodiments herein. The medical device system 400 can include an implantable medical device 402 and one or more stimulation leads 440, 446, and 454. In various embodiments, the implantable medical device 402 can include a therapy unit such as a cardiac rhythm management device, including a pacemaker, a cardiac resynchronization therapy (CRT) device, a remodeling control therapy (RCT) device, a cardioverter/defibrillator, or a device providing two or more of these therapies. In some embodiments, the implantable medical device 402 can be, or also include, a neurological stimulation device. In some embodiments, the implantable medical device 402 can be, or also include, a pharmaceutical delivery device.

The implantable medical device 402 can include a pulse generator housing 404 and a header 408. The term "pulse generator housing" as used herein shall refer to the part or parts of an implanted medical device, such as a cardiac rhythm management device, neurological therapy device, or pharmaceutical delivery device containing the power source and circuitry for delivering pacing therapy, electrical stimulation, shock therapy, and/or pharmaceutical therapy. Together, the pulse generator housing 404, the contents therein, and the header assembly 408 can be referred to as a pulse generator. It will be appreciated that embodiments herein can also be used in conjunction with implantable medical devices that may lack pulse generators such as monitoring devices and pharmaceutical delivery devices.

In FIG. 4, the proximal ends of the stimulation leads 440, 446, and 454 are disposed within the header assembly 408. The stimulation leads 440, 446, and 454 can pass to the heart 452 transvenously. In this view, stimulation lead 440 passes into the coronary venous system, stimulation lead 446 passes into the right atrium, and stimulation lead 454 passes into the right ventricle. However, it will be appreciated that stimulation leads can be disposed in various places within or around the heart. Stimulation lead 440 includes a tip electrode 442 and a ring electrode 444. Stimulation leads 446 and 454 also include tip electrodes 450 and 458 and ring electrodes 448 and 456, respectively. It will be appreciated that stimulation leads can include different numbers of electrodes. For example, in some embodiments, a stimulation lead may only include a single electrode and in some embodiments a stimulation lead may include more than two electrodes. Depending on the configuration, the stimulation leads can provide electrical and/or optical communication between the distal ends of the stimulation leads and the pulse generator. In operation, the pulse generator may generate pacing pulses or therapeutic shocks which are delivered to the heart 452 via the electrodes of the stimulation leads. In many embodiments, the stimulation leads include a material that is electrically conductive in order to deliver the pacing pulses or therapeutic shocks.

Figure 5:
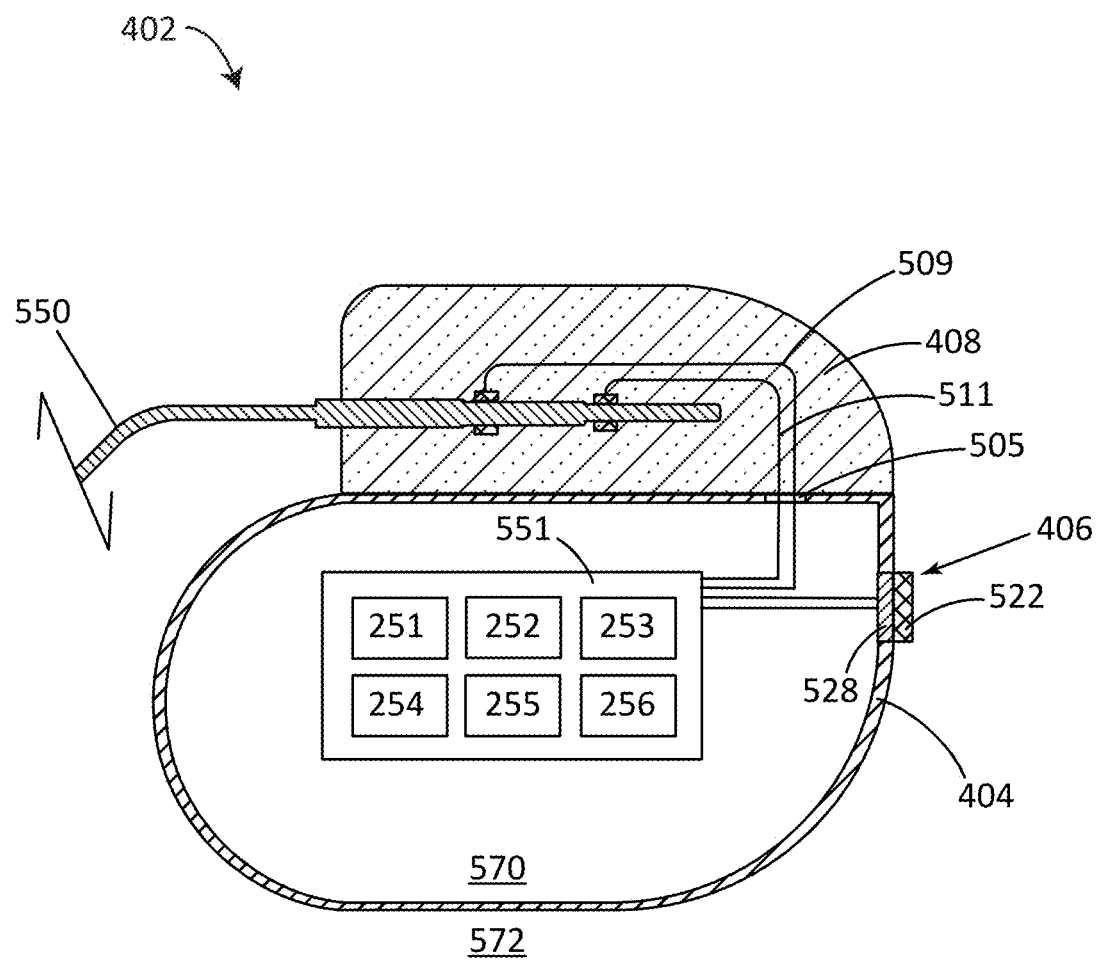
FIG. 5 is a schematic cross-sectional view of the implantable medical device shown in FIG. 4, in accordance with various embodiments herein.

The medical device system 400 can also be configured to sense electrical activity of the heart. By way of example, the medical device system 400 can include an electrical field sensor, such as shown in FIG. 5 as part of control circuitry 551. Specifically, the medical device system 400 can use one or more electrodes, such as the electrodes on the stimulation leads 442, 444, 448, 450, 456, and/or 458, in order to sense electrical activity of the heart, such as a time-varying electrical potential. In some embodiments, the pulse generator housing 404 can serve as an electrode for purposes of sensing electrical activity and/or delivering electrical stimulation.

The medical device system 400 can also include a chemical sensor 406 or an accelerometer 332, or both. The chemical sensor 406 (such as described above in reference to FIG. 1) can be configured to measure the concentration of physiological analytes such as those described below.

Referring now to FIG. 5, a schematic cross-sectional view of an implantable medical device 402, as shown in FIG. 4. The implantable medical device 402 includes a pulse generator housing 404 a header assembly 408. The pulse generator housing 404 of the implantable medical device 402 can include various materials such as metals, polymers, ceramics, and the like. In one embodiment, the pulse generator housing 404 is formed of titanium. The header assembly 408 can be coupled to one or more electrical stimulation leads 550. The header assembly 408 can serve to provide fixation of the proximal end of one or more leads and electrically couples the leads to components within the pulse generator housing 404. The header assembly 408 can be formed of various materials including metals, polymers, ceramics, and the like.

The pulse generator housing 404 defines an interior volume 570 that is hermetically sealed off from the volume 572 outside of the device 500. Various electrical conductors 509, 511 can pass from the header assembly 408 through a feed-through structure 505, and into the interior volume 570. As such, the conductors 509, 511 can serve to provide electrical communication between the electrical stimulation lead 550 and control circuitry 551 disposed within the interior volume 570 of the pulse generator housing 404.

Control circuitry 551 can include many of the same features as those presented above in reference to implantable medical device 102, such as, for example a controller 251, an accelerometer 252, a microprocessor 253, therapy unit circuitry 254, recorder circuitry 255, and sensor interface circuitry 256. In some embodiments, control circuitry 551 can include additional features that are not present in reference to implantable medical device 102. In some embodiments, control circuitry can include fewer features than those presented with respect to implantable medical device 102. The control circuitry 551 can include additional components such memory (such as random access memory (RAM) and/or read only memory (ROM)), a telemetry module, electrical field sensor and stimulation circuitry, a power supply (such as a battery), normalization circuitry, and an optical sensor interface channel, amongst others.

The implantable medical device 402 can also include a chemical sensor 406. In the embodiment shown in FIG. 5, the chemical sensor 406 is a potentiometric chemical sensor. The chemical sensor 406 can specifically include a receptor module 522, and a transducer module 528. The transducer module 528 can be in electrical communication with the control circuitry 551 within the interior volume 570, and in some embodiments, the control circuitry 551 can be configured to selectively activate the chemical sensor (such as, e.g., using the controller 251). In some embodiments, the chemical sensor 406 can be configured to be chronically implanted. In some embodiments, the chemical sensor 406 can be configured to be temporarily implanted.

The chemical sensor 406 can be configured to detect a physiological analyte by exhibiting an electrical signal response to the physiological analyte. In operation, physiological analytes of interest from the in vivo environment can contact the receptor module 522 causing a detectable change in the electrical properties of the same. The transducer module 528 can then be used to process and/or propagate the signal created by the receptor module 522.

Similar to the implantable medical device 102 shown in FIG. 1, the implantable medical device 402 can also include an accelerometer 252. Accelerometer 252 can include a multi-axis accelerometer, such as a 3-axis accelerometer. Accelerometer 252 can be configured to measure position data of a patient. In some embodiments, accelerometer 252 can be configured to assess a preliminary posture of a patient at a given time point. In some embodiments, accelerometer 252 can be configured to assess, in combination with chemical sensor data, a final posture of a patient at a given time point. In some embodiments, accelerometer 252 can be configured to measure multiple position and/or posture variations of a patient over a given time period.

The implantable medical device 402 can incorporate, for example, an electrical field sensor that is configured to generate a signal corresponding to cardiac electric fields. The electrical field sensor can include a first electrode and a second electrode. The electrodes of the electrical field sensor can be the same electrodes used to provide electrical stimulation (such as referred to with respect to FIG. 4) or can be different electrodes. In some embodiments, one or more electrodes can be mounted on one or more electrical stimulation leads 550. In some embodiments, the pulse generator housing 404 can serve as an electrode. The electrodes can be in communication with the electrical field sensor and stimulation circuitry. The electrical field sensor and stimulation circuitry can be used in order to measure the electrical potential difference (voltage) between the first electrode and the second electrode.

Figure 6:
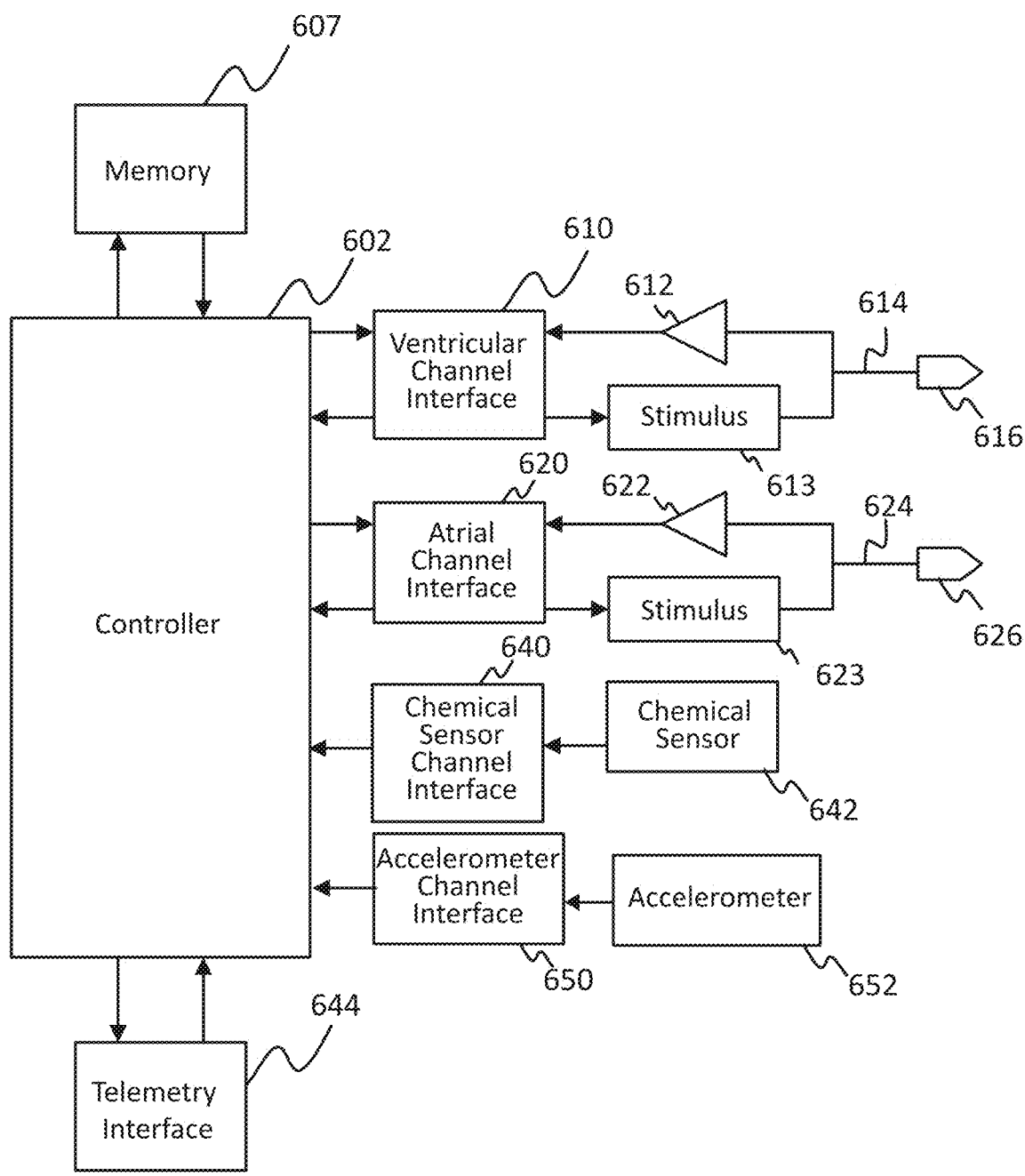
FIG. 6 is a schematic diagram of components of an implantable medical device in accordance with various embodiments herein.

Elements of some embodiments of an implantable medical device 402 are shown in FIG. 6. However, it will be appreciated that some embodiments can include additional elements beyond those shown in FIG. 6. In addition, some embodiments may lack some elements shown in FIG. 6. The implantable medical device 402 can sense cardiac events through one or more sensing channels and outputs pacing pulses to the heart via one or more pacing channels in accordance with a programmed pacing mode. A controller 602 communicates with a memory 607 via a bidirectional data bus. The memory 607 typically comprises read only memory (ROM) or random access memory (RAM) for program storage and RAM for data storage.

The implantable medical device can include atrial sensing and pacing channels comprising at least a first electrode 626, lead 624, sensing amplifier 622, output circuit 623, and an atrial channel interface 620, which can communicate bidirectionally with a port of controller 602. In this embodiment, the device also has ventricular sensing and pacing channels comprising at least a second electrode 616, lead 614, sensing amplifier 612, output circuit 613, and ventricular channel interface 610, which can communicate bidirectionally with a port of controller 602. For each channel, the same lead and electrode are used for both sensing and pacing. The channel interfaces 610 and 620 include analog-to-digital converters for digitizing sensing signal inputs from the sensing amplifiers and registers which can be written to by the control circuitry in order to output pacing pulses, change the pacing pulse amplitude, and adjust the gain and threshold values for the sensing amplifiers. The implantable medical device can also include a chemical sensor 642 and a chemical sensor channel interface 640, and an accelerometer 652 and an accelerometer channel interface 650. A telemetry interface 644 is also provided for communicating with an external programmer.

Figure 7:
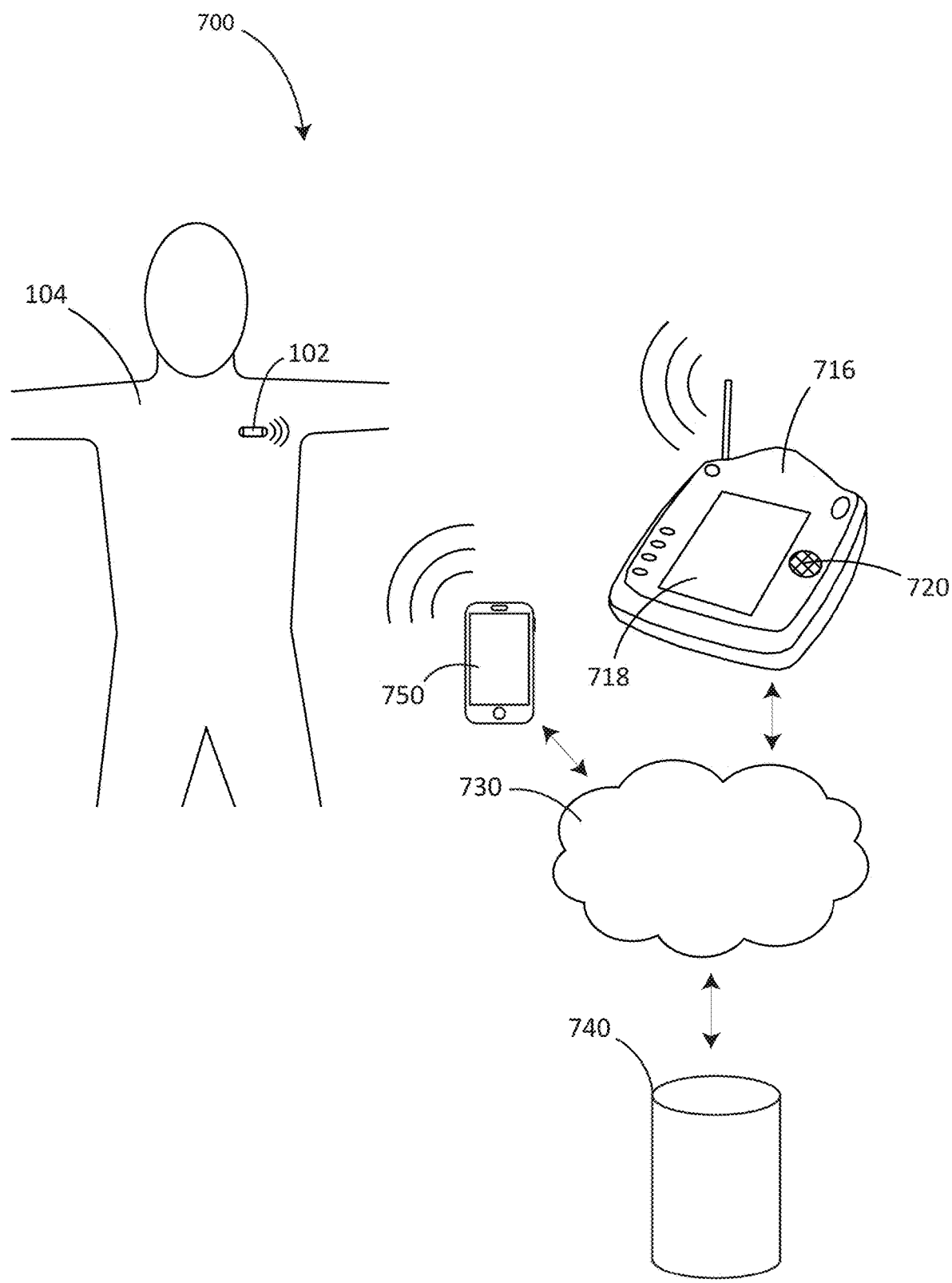
FIG. 7 is a schematic view of a medical device system in accordance with various embodiments herein.

Referring now to FIG. 7, a schematic view is shown of a medical device system 700 in accordance with various embodiments herein. In some embodiments, medical device system 700 can include an implantable medical device 102 such as an implantable loop recorder, implantable monitor device, a cardiac rhythm management device (such as a pacemaker, a cardiac resynchronization therapy (CRT) device, a remodeling control therapy (RCT) device, a cardioverter/defibrillator, or a pacemaker-cardioverter/defibrillator), a neurostimulator device, a pharmaceutical delivery device, or the like. The implantable medical device 102 can be implanted within the body of a patient 104. Various implant sites can be used including, but not limited to, the upper torso, the abdominal area, and the like. In some embodiments, the medical device system can include one or more additional medical devices that are communicatively coupled to one another.

The medical device system 700 can also include an external interface device 716. The external interface device 716 can include a visual display 718 and/or an audio output 720. The external interface device 716 can communicate with the implantable device 102 wirelessly. The external interface device 716 can take on many different forms. In some embodiments, the external interface device 716 can include a programmer or programmer/recorder/monitor device. In some embodiments, the external interface device 716 can include a patient management system. An exemplary patient management system is the LATITUDE® patient management system, commercially available from Boston Scientific Corporation, Natick, MA. Aspects of an exemplary patient management system are described in U.S. Pat. No. 6,978,182, the contents of which are herein incorporated by reference. In some embodiments, the external interface device 716 can include a hand-held monitoring device, a computer, a mobile phone, and the like.

The visual display 718 can include a display that is configured to show the posture determination of a patient. In some embodiments, the video display unit 718 can include a display that is configured to show the posture determination of a patient as a time trend. In some embodiments, the video display unit 718 can include a display that is configured to show the posture determination of a patient along with at least one of a physiological parameter, a therapy dose, or a time of day. The visual display 718 can be a touch screen, computer monitor screen, a mobile device screen, a television screen, and the like. The visual display 718 can include a display that is configured to be an interactive display for use by an authenticated user of the medical device system. In some embodiments, the interactive display can include a web browser, a stand-alone application, and the like.

In some embodiments, the external interface device 716 can send and/or receive data through a data network 730 such as the Internet or a private data network. Through the data network 730, the external interface device 716 can send to and/or receive data from a remote patient management system 740 which can include one or more servers (physical or virtual), databases, and user interfaces. Data can be sent or received through data network 730 via wireless communications or wired communications.

In some embodiments implantable medical device 102 can send or receive data directly to or from a handheld device 750 or other devices such as a desktop computer, laptop computer, other external device, or display or monitor devices. In other embodiments handheld device 750 receives or sends data from or to implantable medical device 102 via external interface device 716 and data network 730. Handheld device 750 may be, for example, a smartphone, cellular phone or a device specifically made to interface with handheld device 750.

Patient management system 740 or handheld device 750 may be used by a patient, a healthcare professional or a caregiver such as a family member. In an embodiment patient management system 740 or handheld device 750 may be used in a mode wherein only display of information from implantable medical device 102 is available. In another embodiment patient management system 740 or handheld device 750 may be used in a mode wherein both display of data from, and programming of parameters within, implantable medical device 102 are available. In an embodiment, handheld device 750 may be used to trigger data storage within implantable medical device 102. In an embodiment the functionality of patient management system 740 or handheld device 750 is configured for a healthcare professional wherein, for example, healthcare functionality provides broad access to data and programming. In another embodiment the functionality of patient management system 740 or handheld device 750 are configured for a patient wherein, for example, healthcare patient functionality provides limited access to data and programming.

Figure 8:
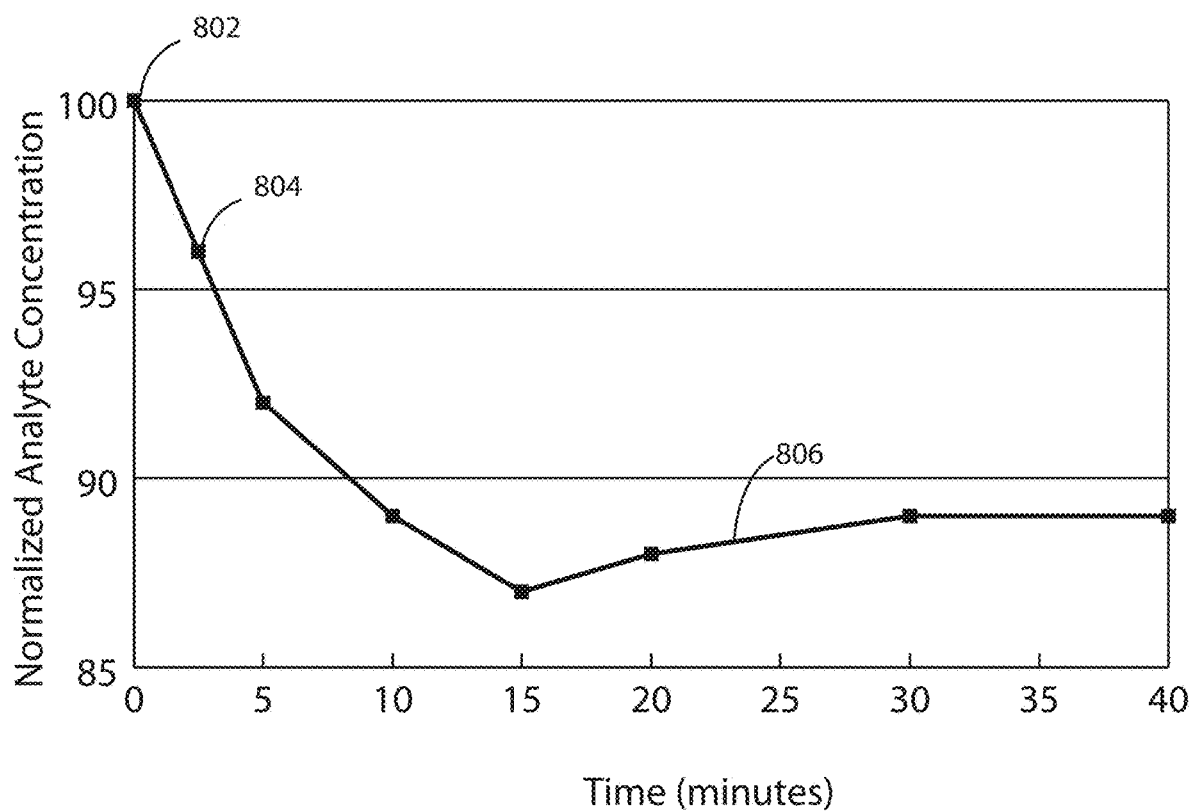
FIG. 8 is a graph of the change in concentration of a simulated physiological analyte as a function of time and posture in accordance with the various embodiments herein.

Referring now to FIG. 8, a change in a physiological analyte is shown as a function of time as a simulated patient moves from a standing posture to a recumbent (or lying down) posture in accordance with the embodiments herein. At time zero, the simulated concentration of a patient's physiological analyte of interest was recorded at data point 802 following a prolonged period of standing. After sampling the patient's physiological analyte at time zero, the patient was placed in a recumbent (or lying down) posture and the concentration of the patient's physiological analyte of interest was monitored as a function of time in the recumbent posture. A noticeable decrease in analyte occurred upon transitioning that patient from a standing posture to a recumbent posture, as reflected in data point 804. In some cases, the change (decrease or increase) in analyte concentration can be observed as quickly as 30 seconds, 60 seconds, 2 minutes, 5 minutes, 10 minutes, 15 minutes, 30 minutes, 60 minutes, 120 minutes, or falling within a range of times between any of the foregoing.

In this example, the decrease in physiological analyte as a function of being recumbent is observed until about 24 minutes at time point 806 wherein the analyte level reaches a plateau and remains consistent as the patient remains in the recumbent posture.

Figure 9:
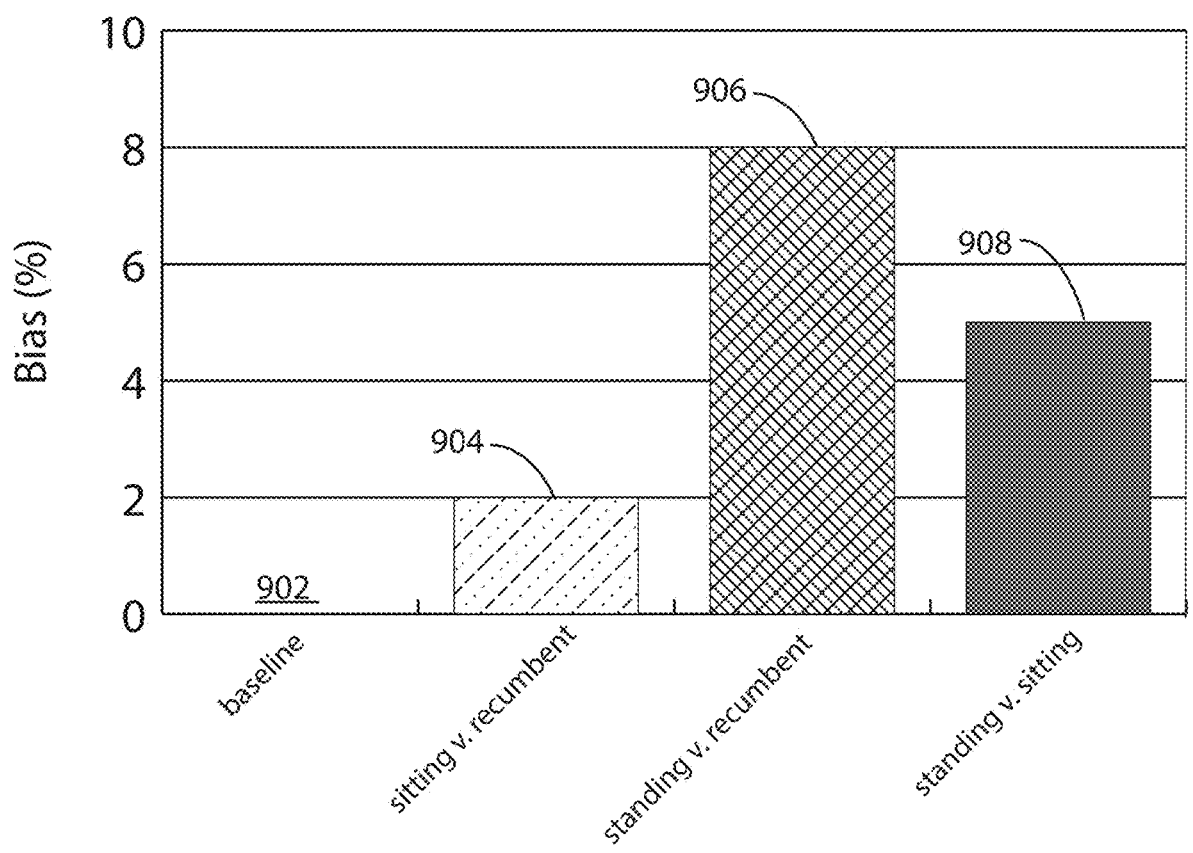
FIG. 9 is a graph of change in concentration of a simulated physiological analyte as a function of various postures in accordance with the various embodiments herein

Similarly, referring now to FIG. 9, a simulated change in concentration of a physiological analyte as a function of various postures is shown in accordance with the embodiments herein. In this example, the concentration of the physiological analyte increases by about 2% as compared to the baseline value 902 when a patient transitions from a recumbent to a sitting posture at 904. Likewise, the concentration of the physiological analyte increases by about 8% as compared to the baseline value 902 when a patient transitions from a recumbent to a standing posture at 906. Interestingly, the concentration of the physiological analyte increases by about 5% as compared to the baseline value 902 when a patient transitions from a sitting to a standing posture at 908. The transitions suggest that patient posture has a significant influence over the reported value of a physiological analyte.

Accelerometers

Accelerometers can be used to help differentiate a patient's posture through a range of positions of a patient's body in space. Accelerometers can include sensors that can be configured to detect, determine, or differentiate between patient positions, such as for example between a vertically oriented position (standing or sitting postures) vs. a horizontally oriented position (lying down or recumbent posture). Exemplary accelerometers can include a 3-axis accelerometer, configured to provide positional orientation information about whether the patient is vertically or horizontally oriented. Exemplary accelerometers suitable for use herein can include capacitive or piezoresistive accelerometers that are configured to measure gravity as well as vibration, shock, or any other type of acceleration.

In some embodiments, the rate of position and/or posture change can also be determined by using accelerometers as a function of time. In general, the rate of position and/or posture change can be determined by analyzing time data along with position data. Exemplary accelerometers can be configured to provide information about the rate of posture change by including time data along with position data, amongst other approaches. Aspects of accelerometers are described in U.S. Pat. Nos. 6,466,821; 7,471,290; and 8,165,840, the content of which is herein incorporated by reference.

Chemical Sensors

Chemical sensors herein can be of various types. In some embodiments, the physiological concentration of an analyte is sensed directly. In other embodiments, the physiological concentration of an analyte is sensed indirectly. By way of example, a metabolite of a particular analyte can be sensed instead of the particular analyte itself. In other embodiments, an analyte can be chemically converted into another form in order to make the process of detection easier. By way of example, an enzyme can be used to convert an analyte into another compound that is easier to detect. For example, the hydrolysis of creatinine into ammonia and N-methyl hydantoin can be catalyzed by creatinine deiminase and the resulting ammonia can be detected by a chemical sensor.

In some embodiments, chemical sensors herein can include at least two functional elements: a receptor and a transducer. It will be appreciated that other elements can also be included. The receptor part of a chemical sensor can transform chemical information into a form of energy or signal that can be measured by the transducer. The transducer can transform and/or convey the energy or signal carrying the chemical information so as to provide a useful analytical signal.

Chemical sensors can include optical devices that utilize changes of optical phenomena or properties at one or more wavelengths, which are the result of an interaction of the analyte with the receptor part of the sensor. Such optical properties can include: absorbance, caused by the absorptivity of the analyte itself or by a reaction with some suitable indicator; reflectance, using a bodily component, tissue, or fluid, or using an immobilized indicator; luminescence, based on the measurement of the intensity of light emitted by a chemical reaction in the receptor system; fluorescence, measured as the positive emission effect caused by irradiation or selective quenching of fluorescence; refractive index, measured as the result of a change in solution composition, in some cases including surface plasmon resonance effects; optothermal effects, based on a measurement of the thermal effect caused by light absorption; light scattering; or the like. In some embodiments, optical chemical sensors can include an optode.

Chemical sensors can also include electrochemical devices that transform the effect of the electrochemical interaction between an analyte and an electrode into a useful signal. Such sensors can include voltammetric sensors, including amperometric devices. Also included are sensors based on chemically inert electrodes, chemically active electrodes and modified electrodes. Also included are sensors with and without (galvanic sensors) a current source. Sensors can also include potentiometric sensors, in which the potential of the indicator electrode (ion-selective electrode, redox electrode, metal oxide electrode, or the like) is measured against a reference electrode. Sensors can include chemically sensitized field effect transistors (CHEMFET) in which the effect of the interaction between the analyte and the active coating is transformed into a change of the source-drain current. Sensors can include potentiometric solid electrolyte gas sensors.

Chemical sensors can also include electrical devices based on measurements, where no electrochemical processes take place, but the signal arises from the change of electrical properties caused by interaction with the analyte. Such sensors can include metal oxide semiconductor sensors based on reversible redox processes of analyte gas components, organic semiconductor sensors, based on the formation of charge transfer complexes, which modify the charge carrier density, electrolytic conductivity sensors, and electric permittivity sensors.

Chemical sensors can also include mass sensitive devices that transform the mass change at a specially modified surface into a change of a property of the support material. The mass change can be caused by accumulation of the analyte. Such sensors can include piezoelectric devices based on the measurement the frequency change of the quartz oscillator plate caused by adsorption of a mass of the analyte at the oscillator and surface acoustic wave devices that depend on the modification of the propagation velocity of a generated acoustical wave affected by the deposition of a definite mass of the analyte.

Chemical sensors can also include magnetic devices based on the change of paramagnetic properties of a gas being analyzed. Chemical sensors can also include thermometric devices based on the measurement of the heat effects of a specific chemical reaction or adsorption that involves the analyte.

In one example of the operation of an optical chemical sensor, analytes of interest from the in vivo environment can diffuse into a chemical sensing element causing a detectable change in the optical properties of the chemical sensing element. Light can be generated by an optical excitation device or emitter, such as an LED or similar device, and can pass through the optical window and into the chemical sensing element. Light can then either be preferentially reflected from or re-emitted by the chemical sensing element proportionally to the sensed analyte and pass back through the optical window before being received by a light detection device or receiver, such as a charge-coupled device (CCD), a photodiode, a junction field effect transistor (JFET) type optical sensor, of complementary metal-oxide semiconductor (CMOS) type optical sensor. Various aspects of exemplary chemical sensors are described in greater detail in U.S. Pat. No. 7,809,441, the content of which is herein incorporated by reference in its entirety.

In another example of the operation of an optical chemical sensor, the optical properties of a tissue or fluid in the body can be directly analyzed. By way of example, light can be generated by an optical excitation device that can be delivered to a component, tissue, or fluid in the body and a light detection device can be used to sense an optical property of the light that has interfaced with the component, tissue, or fluid.

Physiological Analytes

Examples of physiological analytes that can be measured in accordance with chemical sensors of embodiments herein can include physiological analytes such as, but not limited to, electrolytes, proteins, sugars, hormones, peptides, amino acids, metabolites, and the like. In some embodiments, the electrolytes that can be measured can include potassium, calcium, sodium, magnesium, hydrogen phosphate, chloride, bicarbonate, and the like.

Chemical sensors herein can be directed at a specific physiological analyte or a plurality of different physiological analytes. In an embodiment, the physiological analyte sensed can be one or more physiological analytes relevant to cardiac health. In an embodiment, the physiological analyte sensed can be one or more analytes indicative of renal health. In an embodiment, the physiological analyte sensed can be one or more analytes indicative of pulmonary health. In an embodiment, the physiological analyte sensed can be one or more analytes indicative of neuronal health. The physiological analyte sensed can be an ion or a non-ion. The physiological analyte sensed can be a cation or an anion.

Specific examples of physiological analytes that can be sensed include acetic acid (acetate), aconitic acid (aconitate), ammonium, hemoglobin, blood urea nitrogen (BUN), B-type natriuretic peptide (BNP), bromate, calcium, carbon dioxide, cardiac specific troponin, chloride, choline, citric acid (citrate), cortisol, copper, creatinine, creatinine kinase, fluoride, formic acid (formate), glucose, hydronium ion, isocitrate, lactic acid (lactate), lithium, magnesium, maleic acid (maleate), malonic acid (malonate), myoglobin, nitrate, nitric-oxide, oxalic acid (oxalate), oxygen, phosphate, phthalate, potassium, pyruvic acid (pyruvate), selenite, sodium, sulfate, urea, uric acid, and zinc. Inorganic cations sensed by this method include but not limited to hydronium ion, lithium ion, sodium ion, potassium ion, magnesium ion, calcium ion, silver ion, zinc ion, mercury ion, lead ion and ammonium ion. Inorganic anions sensed by this method include but not limited to carbonate anion, nitrate anion, sulfite anion, chloride anion and iodide anion. Organic cations sensed by this method include but are not limited to norephedrine, ephedrine, amphetamine, procaine, prilocaine, lidocaine, bupivacaine, lignocaine, creatinine and protamine. Organic anions sensed by this method include but not limited to salicylate, phthalate, maleate, and heparin. Neutral analytes sensed by this method include but not limited to ammonia, ethanol, and organic amines. In an embodiment, ions that can be sensed include potassium, sodium, chloride, calcium, and hydronium (pH). In a particular embodiment, concentrations of both sodium and potassium are measured. In another embodiment, concentrations of both magnesium and potassium are measured.

In some embodiments, the physiological analytes can specifically include one or more of sodium ion, magnesium ion, chloride ion, calcium ion, carbonate ion, phosphate ion, sulfate ion, insulin, aldosterone, troponin, glucose, creatinine, and BNP.

In some embodiments, the analytes can specifically include one or more of partial pressure of oxygen ($PaO_2$), partial pressure of carbon dioxide ($PaCO_2$) and oxygen saturation ($O_2Sat$).

Posture Determination and Data Normalization

In the embodiments herein, position data measured by an accelerometer and physiological analyte data measured by a chemical sensor can be utilized together to make a posture determination of a patient. In the embodiments herein, position data measured by an accelerometer and physiological analyte data measured by a chemical sensor can be utilized together to classify the patient as being in a sitting, standing or lying down (recumbent) posture. In some embodiments, position data measured by an accelerometer and physiological analyte data measured by a chemical sensor can be utilized together to classify the patient as being in one of a sitting posture, standing posture, lying down (or recumbent) posture, or an indeterminate posture. Accelerometer data alone is typically insufficient to differentiate between a sitting and standing posture because they can both be vertically oriented positions. However, an analysis of preliminary position and/or posture data and physiological analyte data, can be performed by a controller in the medical device system to make a final posture determination of the patient. The combined data analysis can provide information to disambiguate a sitting or standing posture of a patient.

The medical device system can be configured to display the posture determination of a patient on a visual display. In some embodiments, the posture determination can be displayed along with a physiological parameter, a therapy type, a therapy dose, and a time of day. In some embodiments, the visual display can be interactive with an authorized user.

In some embodiments, physiological signals measured by a chemical sensor can be normalized with respect to posture determination. Various embodiments herein can include normalization circuitry and/or execute an operation of normalization. It will be appreciated that normalization can include various steps. As such, normalization circuitry or modules herein can execute a number of specific steps.

In some embodiments, normalization can include modifying the value of chemical sensor data as a function of posture, and create corrected or normalized chemical sensor data that more reliably reflects the actual physiological signal with respect to posture. By way of example, the normalization circuitry or module can take native (or raw) data as provided by the chemical sensor and then modify the same by doing at least one of increasing, decreasing, or maintaining the values thereof in order to result in normalized (or corrected) data.

In some embodiments, correcting the native or raw data can be performed in a manner that is proportional to the position changes indicated by the accelerometer data. Such proportionality can include linear, exponential, or logarithmic proportionality. A baseline value for the accelerometer can be set or can be derived from evaluation of the accelerometer data over time. Then, to normalize pieces of the chemical sensor data, the corresponding chemical sensor data can be compared to the baseline values and the difference can be used to determine what changes to make to the chemical sensor data in a proportional manner. In some embodiments, the baseline values can be from evaluating accelerometer data for the particular patient into which the device or system is implanted. In other embodiments, the baseline values can be from evaluating accelerometer data for a class of similar patients (such as one or more of age, sex, diagnosis, disease progression, etc.).

In some embodiments, correcting the native or raw data can be performed by applying a function that is derived through analysis of a training set of data. The training set of data can come from the particular patient into which the device or system is implanted or from other patients, such as other similar patients. In one approach, the function can be derived by first observing the relationship between positional and/or postural change and chemical sensor data change by having the patient, or a class of patients, assume various activity levels, postures, and the like, and observing the resulting chemical sensor values. Many different techniques can be used. In some embodiments, a best-fit algorithm can be used to derive a function that describes the relationship between changes in accelerometer data and chemical sensor data. Once such a function is derived, it can be used to generate normalized or corrected chemical sensor data based upon raw chemical sensor data and accelerometer data input.

In some embodiments, normalizing the native or raw data can be performed by matching the accelerometer data to a corresponding template providing specific procedures for the correction chemical sensor data and then following such procedures. By way of example, in some embodiments, the device or system can include templates corresponding to different specific postures. Posture templates can include a lying down (or recumbent) posture template, a sitting (or seated) posture template, and a standing posture template (many other postures can also be used). Similar templates can be used for activity monitoring, respiration monitoring, and the like. After matching the accelerometer data to a corresponding template, the specific procedures described by the same can be executed in order to generate normalized or corrected chemical sensor data.

In some embodiments, normalization of data can include discarding or otherwise not acting upon native or raw data provided by a chemical sensor corresponding to times when the accelerometer data and/or posture determination (or optionally other sensor data) indicates that the chemical sensor data may not be reliable. As an example, in some embodiments the normalization circuitry can suspend chemical sensor data collection and/or reporting for predetermined postures, predetermined activity values, or predetermined respiration values. In some embodiments the normalization circuitry will not use or will omit chemical sensor data for predetermined postures, predetermined positions, predetermined activity values, or predetermined respiration values. In some embodiments, the normalization circuitry will suspend chemical sensor data collection or not use the chemical sensor data for a predetermined length of time after a posture change, activity level change, or respiration change. In some embodiments, chemical sensor data is stored and/or displayed based on corresponding posture data, corresponding position data, corresponding activity data, and/or corresponding respiration data.

In some embodiments, the normalization circuitry can affect how alerts are issued by the device or system, or by how an external system interprets the chemical sensor data for purposes of issuing alerts. It will be appreciated that in various embodiments, the device or system can be configured to issue an alert (which could show up on an external interface device or visual display, or could pass through a data network to a remote patient management system). The alert can regard the levels of physiological analytes measured by the chemical sensor(s). However, in some embodiments, the issuance of an alert can be dependent on the postural and/or positional data corresponding to the chemical sensor data. In some embodiments, the issuance of an alert can also include data regarding the posture determination of a patient such that the alert can be acted upon or not in consideration of the corresponding posture determination of a patient.

As an example, a system can be configured to issue alerts for potassium levels that are too high (hyperkalemia alerts) and/or alerts for potassium levels that are too low (hypokalemia alerts). Similarly, the system can be configured to issue alerts for other physiological analyte levels that are too high (hyper alerts) and/or alerts for analyte levels that are too low (hypo alerts). In some embodiments, normalization can include selecting appropriate ranges and/or threshold values (from preselected values or determined dynamically) for physiological analytes based on the patient's posture determination.

Various aspects of normalizing chemical sensor data are described in greater detail in co-pending U.S. Pat. App. No. 2016/0374597A1, the content of which is herein incorporated by reference in its entirety.

Physiological Parameters and Targeted Therapies

The medical systems embodied herein can detect a physiological parameter in conjunction with posture determination. Exemplary physiological parameters can include cardiac, pulmonary, renal, nervous, etc. In some embodiments, a physiological parameter can be used in conjunction with a posture determination of a patient to determine a course of treatment or a modification of treatment using targeted therapies. In some embodiments, a response of a particular physiological parameter can be quantified in response to a sitting-to-standing transition. For example, a pre-transition posture determination can be made at an initial time just prior to when a patient transitions into a standing posture by recording accelerometer data and chemical sensor data. Upon standing, a post-transition posture determination can be made by recording a second set of accelerometer data and chemical sensor data. The change in chemical sensor data as a function of posture can be measured to reflect that transition.

Suitable targeted therapies as discussed herein can include electrical stimulation, pharmaceutical delivery, etc. In some embodiments, a therapy can be optimized while the patient is in a sitting posture. In some embodiments, a therapy can be optimized while the patient is in a standing posture.

In some embodiments, a physiological parameter can be displayed within the medical device system on a visual display. In some embodiments, the physiological parameter can be displayed as a function of the posture determination of a patient. The physiological parameter can additionally be collected, aggregated, and/or displayed only for time periods when the patient is in a specified set of determined postures.

Methods

Figure 10:
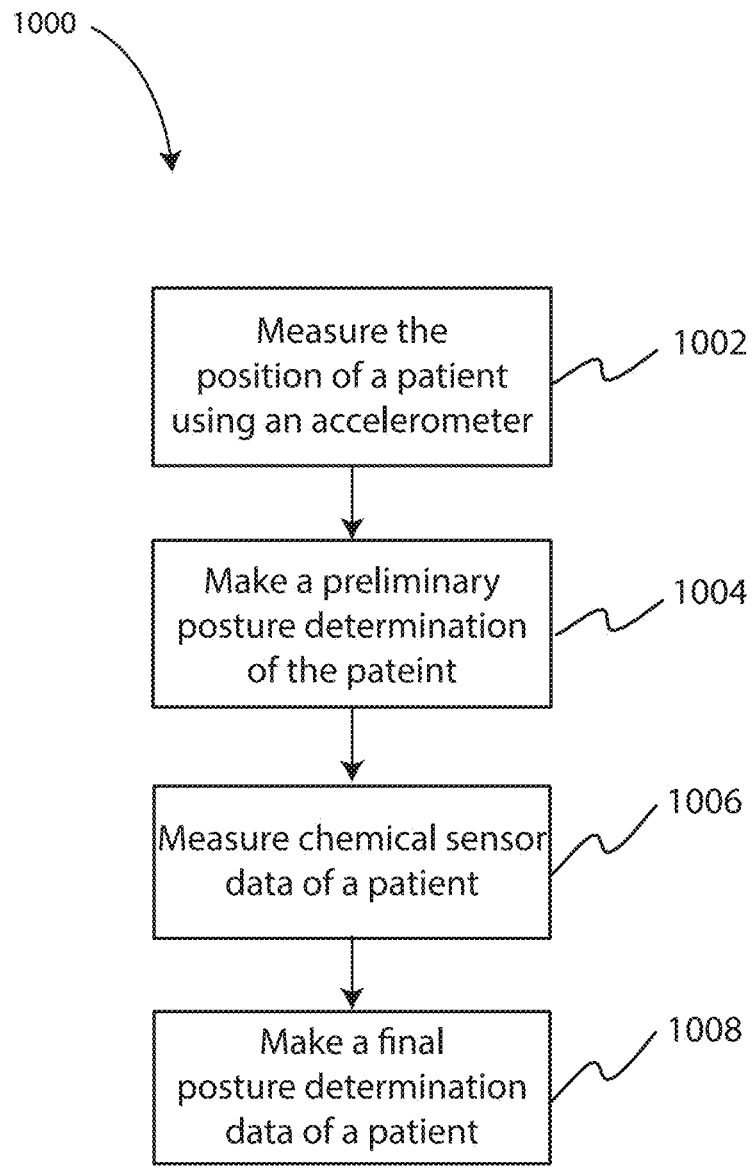
FIG. 10 is a flowchart showing operations that can be performed in accordance with various embodiments herein.

Embodiments herein can include various methods. Exemplary methods can include any of the approaches and/or operations described above. In an embodiment, a method for operating a medical device system is included. Referring now to FIG. 10, the method 1000 can include an operation of measuring position of a patient using an accelerometer at 1002. The method can also include an operation of making a preliminary posture determination of a patient using data measured by an accelerometer at 1004. The method can also include measuring chemical data of a patient using a chemical sensor at 1006. The method can also include making a final posture determination of a patient using data measured by an accelerometer and data measured by a chemical sensor, using a controller at 1008. In some embodiments, methods herein can also include reporting the posture of the patient and/or providing the posture of the patient to a different circuit or component as an input for further processing.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein. As such, the embodiments described herein are not intended to be exhaustive or to limit the invention to the precise forms disclosed in the detailed description. Rather, the embodiments are chosen and described so that others skilled in the art can appreciate and understand the principles and practices.

The invention claimed is:

1. A method of operating a medical device system comprising:
   measuring position data using an accelerometer;
   making a preliminary posture determination of a patient using the position data measured by the accelerometer;
   when the preliminary posture determination does not indicate a recumbent posture, then:,
      measuring chemical data using an optical chemical sensor; and
      normalizing the chemical data by correcting the chemical data in a manner that is proportional to the position data indicated by the accelerometer; and
   making a final posture determination of the patient using the position data measured by the accelerometer and the normalized chemical data measured by the optical chemical sensor;
   wherein the accelerometer and the optical chemical sensor are disposed within a housing of an implantable medical device.

2. The method of claim 1, further comprising activating the optical chemical sensor if the preliminary posture determination does not indicate the recumbent posture.

* * * * *